(12) United States Patent
Kim et al.

(10) Patent No.: US 10,575,741 B2
(45) Date of Patent: Mar. 3, 2020

(54) WEARABLE BIOMETRIC INFORMATION MEASUREMENT DEVICE

(71) Applicant: Samsung Electronics Co., Ltd., Gyeonggi-do (KR)

(72) Inventors: Jae-Hong Kim, Incheon (KR); Jea-Hyuck Lee, Gyeonggi-do (KR); Jin-Hong Min, Gyeonggi-do (KR); Jae-Geol Cho, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 1137 days.

(21) Appl. No.: 14/829,261

(22) Filed: Aug. 18, 2015

(65) Prior Publication Data
US 2016/0045135 A1  Feb. 18, 2016

(30) Foreign Application Priority Data

Aug. 18, 2014 (KR) .................. 10-2014-0107298
Jul. 17, 2015 (KR) .................. 10-2015-0101727

(51) Int. Cl.
*A61B 5/0408* (2006.01)
*A61B 5/00* (2006.01)
(Continued)

(52) U.S. Cl.
CPC ...... *A61B 5/04085* (2013.01); *A61B 5/02444* (2013.01); *A61B 5/044* (2013.01);
(Continued)

(58) Field of Classification Search
CPC ............ A61B 5/04085; A61B 5/04087; A61B 5/6833; A61B 5/6832; A61B 5/6835; A61B 2562/16; A61B 2562/166
(Continued)

(56) References Cited

U.S. PATENT DOCUMENTS 4,706,680 A * 11/1987 Keusch ................ A61B 5/0408
128/207.15
4,889,131 A * 12/1989 Salem .................. A61B 5/0006
600/484

(Continued)

FOREIGN PATENT DOCUMENTS

CN   103025233   4/2013
CN   203662727   6/2014
(Continued)

OTHER PUBLICATIONS

International Search Report dated Nov. 25, 2015 issued in counterpart application No. PCT/KR2015/008603, 8 pages.
(Continued)

*Primary Examiner* — Lee S Cohen
*Assistant Examiner* — Erin M Cardinal
(74) *Attorney, Agent, or Firm* — The Farrell Law Firm, P.C.

(57) ABSTRACT

A biometric information measurement device is provided. The device includes a substrate unit including components required for operation of the biometric information measurement device, and electrodes for measuring biometric information. The components and the electrodes are disposed on a single side of the substrate unit. The device also includes a case having a first surface and a second surface. The first surface is attached to an attachment pad for attaching the biometric information measurement device to a body, and the second surface faces the single side of the substrate unit. The electrodes are each exposed through respective openings in the first surface.

15 Claims, 31 Drawing Sheets

(51) Int. Cl.
*A61B 5/044* (2006.01)
*A61B 5/04* (2006.01)
*A61B 5/024* (2006.01)

(52) U.S. Cl.
CPC ...... *A61B 5/04012* (2013.01); *A61B 5/04087* (2013.01); *A61B 5/4812* (2013.01); *A61B 5/6833* (2013.01); *A61B 5/6843* (2013.01); *A61B 5/7475* (2013.01); *A61B 2560/0468* (2013.01); *A61B 2562/04* (2013.01); *A61B 2562/043* (2013.01); *A61B 2562/16* (2013.01); *A61B 2562/166* (2013.01)

(58) Field of Classification Search
USPC .................................................. 600/391–392
See application file for complete search history.

(56) References Cited

U.S. PATENT DOCUMENTS

| | | | | |
|---|---|---|---|---|
| 5,465,727 | A * | 11/1995 | Reinhold, Jr. | A61B 5/04085 128/904 |
| 7,970,450 | B2 | 6/2011 | Kroecker et al. | |
| 8,483,809 | B2 | 7/2013 | Kim et al. | |
| 8,606,353 | B2 | 12/2013 | Yeo et al. | |
| 8,613,708 | B2 | 12/2013 | Bishay et al. | |
| 2003/0149349 | A1 * | 8/2003 | Jensen | A61B 5/02055 600/372 |
| 2007/0149887 | A1 | 6/2007 | Hwang et al. | |
| 2007/0255184 | A1 * | 11/2007 | Shennib | A61B 5/0006 600/591 |
| 2008/0288026 | A1 * | 11/2008 | Cross | A61B 5/0408 607/60 |
| 2010/0125190 | A1 * | 5/2010 | Fadem | A61B 5/0478 600/383 |
| 2010/0234716 | A1 * | 9/2010 | Engel | A61B 5/02055 600/391 |
| 2010/0298687 | A1 * | 11/2010 | Yoo | A61B 5/0006 600/391 |
| 2011/0009729 | A1 | 1/2011 | Shin et al. | |
| 2012/0088999 | A1 | 4/2012 | Bishay et al. | |
| 2012/0089037 | A1 | 4/2012 | Bishay | |
| 2013/0116534 | A1 | 5/2013 | Woo | |
| 2013/0172691 | A1 | 7/2013 | Tran | |
| 2013/0225967 | A1 * | 8/2013 | Esposito | A61B 5/0404 600/392 |
| 2014/0073883 | A1 | 3/2014 | Rao et al. | |
| 2014/0100432 | A1 | 4/2014 | Golda et al. | |
| 2014/0123912 | A1 * | 5/2014 | Menkes | A61B 5/1105 119/859 |
| 2014/0206976 | A1 * | 7/2014 | Thompson | A61B 5/0006 600/391 |
| 2014/0213878 | A1 | 7/2014 | Banet et al. | |
| 2015/0112176 | A1 | 4/2015 | Sano et al. | |
| 2015/0141791 | A1 | 5/2015 | O'Neill et al. | |
| 2015/0281424 | A1 * | 10/2015 | Vock | A43B 3/0005 455/418 |
| 2015/0351689 | A1 * | 12/2015 | Adams | A61B 5/6833 600/300 |
| 2016/0113544 | A1 * | 4/2016 | Li | A61B 5/6833 600/391 |
| 2016/0165719 | A1 * | 6/2016 | Li | H05K 1/0283 361/749 |

FOREIGN PATENT DOCUMENTS

| | | | |
|---|---|---|---|
| DE | 202016105483 U1 * | 10/2016 | ............... A61B 5/01 |
| JP | 2007167448 | 7/2007 | |
| JP | 2008-086390 | 4/2008 | |
| KR | 1020030092120 | 12/2003 | |
| KR | 1020050119890 | 12/2005 | |
| KR | 1020070066417 | 6/2007 | |
| KR | 1020080013298 | 2/2008 | |
| KR | 1020090102943 | 10/2009 | |
| KR | 100927471 | 11/2009 | |
| KR | 1020110045658 | 5/2011 | |
| KR | 1020110092863 | 8/2011 | |
| KR | 1020120065540 | 6/2012 | |
| KR | 1020120084950 | 7/2012 | |
| KR | 1020140116347 | 10/2014 | |
| WO | WO 2013/179368 | 12/2013 | |
| WO | WO 2014/116816 | 7/2014 | |

OTHER PUBLICATIONS

European Search Report dated Jun. 8, 2016 issued in counterpart application No. 15181421.7-1657, 11 pages.
Chinese Office Action dated Jun. 13, 2019 issued in counterpart application No. 201510508583.3, 19 pages.
Chinese Office Action dated Jan. 22, 2020 issued in counterpart application No. 201510508583.3, 8 pages.

* cited by examiner

WEARABLE BIOMETRIC INFORMATION MEASUREMENT DEVICE

PRIORITY

This application claims priority under 35 U.S.C. § 119(a) to Korean Patent Application Serial No. 10-2014-0107298, which was filed in the Korean Intellectual Property Office on Aug. 18, 2014, and Korean Patent Application Serial No. 10-2015-0101727, which was filed in the Korean Intellectual Property Office on Jul. 17, 2015, the content of which is incorporated herein by reference.

BACKGROUND OF THE INVENTION

1. Field of the Invention

The present invention relates generally to a wearable device, and more particularly, to a wearable biometric information measurement device that is attached to the user's body for measuring biometric information of the user.

2. Description of the Related Art

There is a growing need for measurement devices that can identify user biometric information, and can manage an individual's health based on the identified biometric information. These measurement devices have been provided in the form of bracelets, arm bands, chest bands, or the like, which can be worn on the user's body to constantly measure biometric information. Various heart rate monitoring products have been created as one type of measurement device. For example, the user's heart rate can be measured through a plurality of electrodes, lead wires, and an electrocardiogram (ECG) measurement device connected with the same. However, such a device can easily loosen or detatch from the user's body as a result of the user's movement, which may cause an error in the ECG measurement. In addition, it is inconvenient for the user to carry the ECG measurement device because the connection between the electrodes, the lead wires, and the ECG measurement device should be maintained all the time. Furthermore, whenever the ECG measurement is performed, the electrodes are required to be attached to the user's body.

In addition, the ECG measurement involves a belt that is worn on the user's chest. However, this belt may easily loosen, or may cause a feeling of tightness around the user's chest.

Moreover, ECG patches have been provided to assist in portability. However, the patches are too big or too thick to be attached to the user's body during user activities, and the attachment of the patches to the body may not be maintained when the user moves.

Conventional devices for measuring biometric information cannot monitor a change in biometric signals according to the user's condition. For example, even though user's heart rate increases and various physical changes occur during exercise, the typical measurement devices record only the biometric information, but cannot obtain accurate physical information on the user. In addition, some users need to measure their biometric information and the physical status 24 hours a day. For example, a user suffering from a heart disease cannot predict a heart attack, so the user needs to measure a change in the biometric information 24 hours a day to inform a third party of the user status information according to the biometric change. In addition, in the case of an irregular heartbeat, the heart rate and the blood pressure of a patient tend to increase while eating a meal. In this case, it needs to be determined if the changes in the heart rate and the blood pressure stem from the meal or from exercise.

SUMMARY

The present invention has been made to address at least the above problems and/or disadvantages and to provide at least the advantages described below. Accordingly, an aspect of the present invention provides a wearable biometric information measurement device that is easy to carry and that is small and light to allow the user to move or work while wearing the device on his or her body.

Another aspect of the present invention provides a wearable biometric information measurement device by which the user can constantly measure his or her health status and biometric information, and if any problem is detected, the user can make an accurate diagnosis through the measured data to thereby take care of his or her health, or observe the prognosis later on.

Another aspect of the present invention provides a wearable biometric information measurement device that the user can easily carry, and that can measure the user biometric information while being in contact with the user's body, allowing the user to perform various physical activities.

Another aspect of the present invention provides a wearable biometric information measurement device that can record the user activities as well as biometric signals by detecting the biometric information according to the user's condition and the user's physical activities.

Another aspect of the present invention provides a wearable biometric information measurement device that analyzes the biometric signals, based on the user's physical activities to provide a healthcare service that is more accurate and suitable for the user.

Another aspect of the present invention provides a wearable biometric information measurement device that can easily measure an ECG, a degree of stress, a breathing rate per minute, sleep stages, sleep patterns, sleep postures, the number of steps, or detection of a fall to thereby allow the user to identify the measurement result.

Another aspect of the present invention provides a wearable biometric information measurement device that can be attached to several positions on the chest of the user, and that is not easily detached during the movement of the user to minimize user inconvenience and obtain accurate measurement data.

Another aspect of the present invention provides a wearable biometric information measurement device that can be attached to the user's body for a long time to thereby monitor the user biometric information 24 hours a day.

Another aspect of the present invention provides a wearable biometric information measurement device that enables information on a patient to be shared with a third party in the case of an emergency in relation to the patient.

Another aspect of the present invention provides a wearable biometric information measurement device that can accurately detect the user biometric information, and that allows the user to recognize errors in detection values of the biometric information measurement device due to, for example, incorrect attachment of the biometric information measurement device, low battery power, or the like.

In accordance with an aspect of the present invention, a biometric information measurement device is provided. The device includes a substrate unit including components required for operation of the biometric information measurement device, and electrodes for measuring biometric information. The components and the electrodes are disposed on a single side of the substrate unit. The device also includes a case having a first surface and a second surface. The first surface is attached to an attachment pad for attaching the biometric information measurement device to a body, and the second surface faces the single side of the substrate unit. The electrodes are each exposed through respective openings in the first surface.

In accordance with another aspect of the present invention, a biometric information measurement device is provided. The device includes a measuring device including a substrate unit on which components, electrodes, and biometric information measurement components are mounted. The measuring device also includes a case that covers the modules, through which the electrodes are exposed, and to which a disposable gel pad is attached. The device also includes a disposable gel pad that is attached to the measuring device. The disposable gel pad includes a pad member having adhesive for attachment to the case and the user's body, and having first openings corresponding to the components and second openings corresponding to the electrodes. The disposable gel pad also includes conductive gel members that are filled in the second openings to make contact between the electrodes and the user's body. The disposable gel pad further includes a mesh member that is provided within the pad member.

In accordance with another aspect of the present disclosure, a method is provided for detecting health status through a biometric information measurement device and an electronic device. Coupling of a disposable gel pad and a biometric information measurement component that includes a substrate unit provided with components and electrodes, is detected. Attachment of the disposable gel pad to a user's body is detected. User biometric information and user status information are detected. Biometric information and user status information are received by the electronic device.

BRIEF DESCRIPTION OF THE DRAWINGS

The above and other aspects, features, and advantages of the present disclosure will be more apparent from the following detailed description when taken in conjunction with the accompanying drawings, in which.

DETAILED DESCRIPTION OF EMBODIMENTS OF THE PRESENT INVENTION

Figure 1:
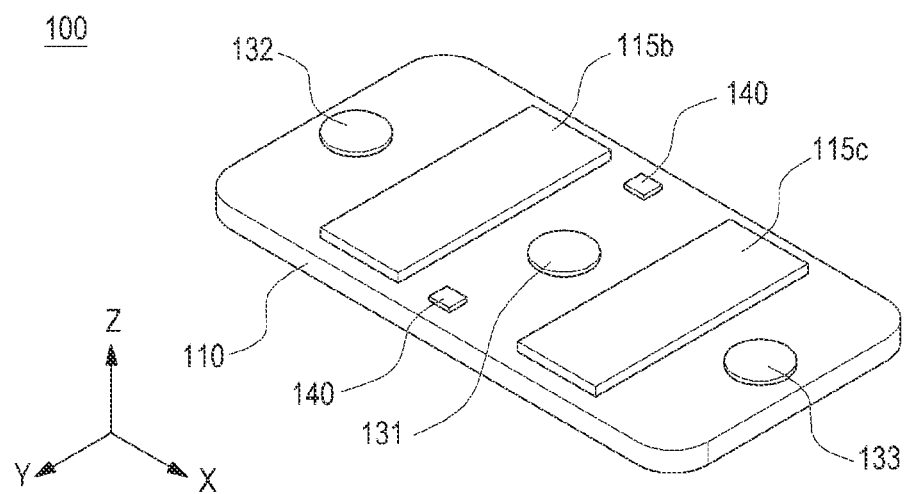
FIG. 1 is a diagram illustrating a wearable biometric information measurement device, according to an embodiment of the present invention.

Embodiments of the present invention are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the present invention.

As used herein, the expressions "include", "may include" and other conjugates refer to the existence of a corresponding function, operation, or constituent element, and do not limit one or more additional functions, operations, or constituent elements. Further, as used herein, the terms "include", "have", and their conjugates are intended merely to denote a certain feature, numeral, step, operation, element, component, or a combination thereof, and should not be construed to exclude the existence of or a possibility of one or more other features, numerals, steps, operations, elements, components, or combinations thereof.

Further, as used herein, the expression "or" includes any or all combinations of words enumerated together. For example, the expression "A or B" may include A, B, or both A and B.

While expressions including ordinal numbers, such as, for example, "first" and "second", as used herein, may modify various constituent elements, such constituent elements are not limited by the above expressions. For example, the above expressions do not limit the sequence and/or importance of the elements. The expressions may be used to distinguish a component element from another component element. For example, a first user device and a second user device indicate different user devices. A first constituent element may be referred to as a second constituent element, and likewise, a second constituent element may also be referred to as a first constituent element without departing from the scope of the embodiments of the present invention.

It should be noted that if it is described that one component element is "coupled" or "connected" to another component element, the first component element may be directly coupled or connected to the second component, or a third component element may be "coupled" or "connected" between the first and second component elements. When one component element is "directly coupled" or "directly connected" to another component element, a third component element does not exist between the first component element and the second component element.

The terms used herein are merely for the purpose of describing particular embodiments and are not intended to limit the embodiments of the present invention. As used herein, singular forms are intended to include plural forms as well, unless the context clearly indicates otherwise.

Unless defined otherwise, all terms used herein, including technical terms and scientific terms, have the same meanings as those commonly understood by a person of ordinary skill in the art to which the embodiments of the present invention pertain. Such terms as those defined in a generally used dictionary are to be interpreted to have the meanings that are the same as the contextual meanings in the relevant field of art, and are not to be interpreted to have ideal or excessively formal meanings, unless clearly defined in the embodiments of the present invention.

An electronic device, according to an embodiment of the present invention, may have a function that is provided through various colors emitted depending on the states of the electronic device, or a function of sensing a gesture or bio-signal. For example, the electronic device may be embodied as at least one of a smart phone, a tablet personal computer (PC), a mobile phone, a video phone, an e-book reader, a desktop PC, a laptop PC, a netbook computer, a personal digital assistant (PDA), a portable multimedia player (PMP), an MP3 player, a mobile medical device, a camera, a wearable device (e.g., a head-mounted-device (HMD) such as, for example, electronic glasses, electronic clothes, an electronic bracelet, an electronic necklace, an electronic appcessory, an electronic tattoo, or a smart watch).

According to an embodiment of the present invention, the electronic device may be a smart home appliance having a function serviced by light that emits various colors depending on the states of the electronic device, or a function of sensing a gesture or bio-signal. The smart home appliance, as an example of the electronic device, may be embodied as at least one of, for example, a television, a digital versatile disc (DVD) player, an audio player, a refrigerator, an air conditioner, a vacuum cleaner, an oven, a microwave oven, a washing machine, an air cleaner, a set-top box, a television (TV) box, a game console, an electronic dictionary, an electronic key, a camcorder, and an electronic picture frame.

According to an embodiment of the present invention, the electronic device may be embodied as at least one of a medical appliance (e.g., magnetic resonance angiography (MRA), magnetic resonance imaging (MRI), computed tomography (CT), and ultrasonic machines), navigation equipment, a global positioning system (GPS) receiver, an event data recorder (EDR), a flight data recorder (FDR), an automotive infotainment device, electronic equipment for ships (e.g., ship navigation equipment and a gyrocompass), avionics, security equipment, a vehicle head unit, an industrial or home robot, an automatic teller machine (ATM) of a banking system, and a point of sales (POS) of a shop.

According to an embodiment of the present invention, the electronic device may be embodied as at least one of a part of furniture or a building/structure, an electronic board, an electronic signature receiving device, a projector, and various kinds of measuring instruments (e.g., a water meter, an electric meter, a gas meter, and a radio wave meter), each of which has a function that is provided through various colors emitted depending on the states of the electronic device or a function of sensing a gesture or bio-signal. The electronic device, according to an embodiment of the present invention may be a combination of one or more of the aforementioned various devices. Further, the electronic device, according to an embodiment of the present invention, may be a flexible device. Further, it will be apparent to those skilled in the art that the electronic device is not limited to the aforementioned devices.

The term "user", as used herein, may indicate a person who uses an electronic device or a device (e.g., an artificial intelligence electronic device) that uses an electronic device.

Figure 2:
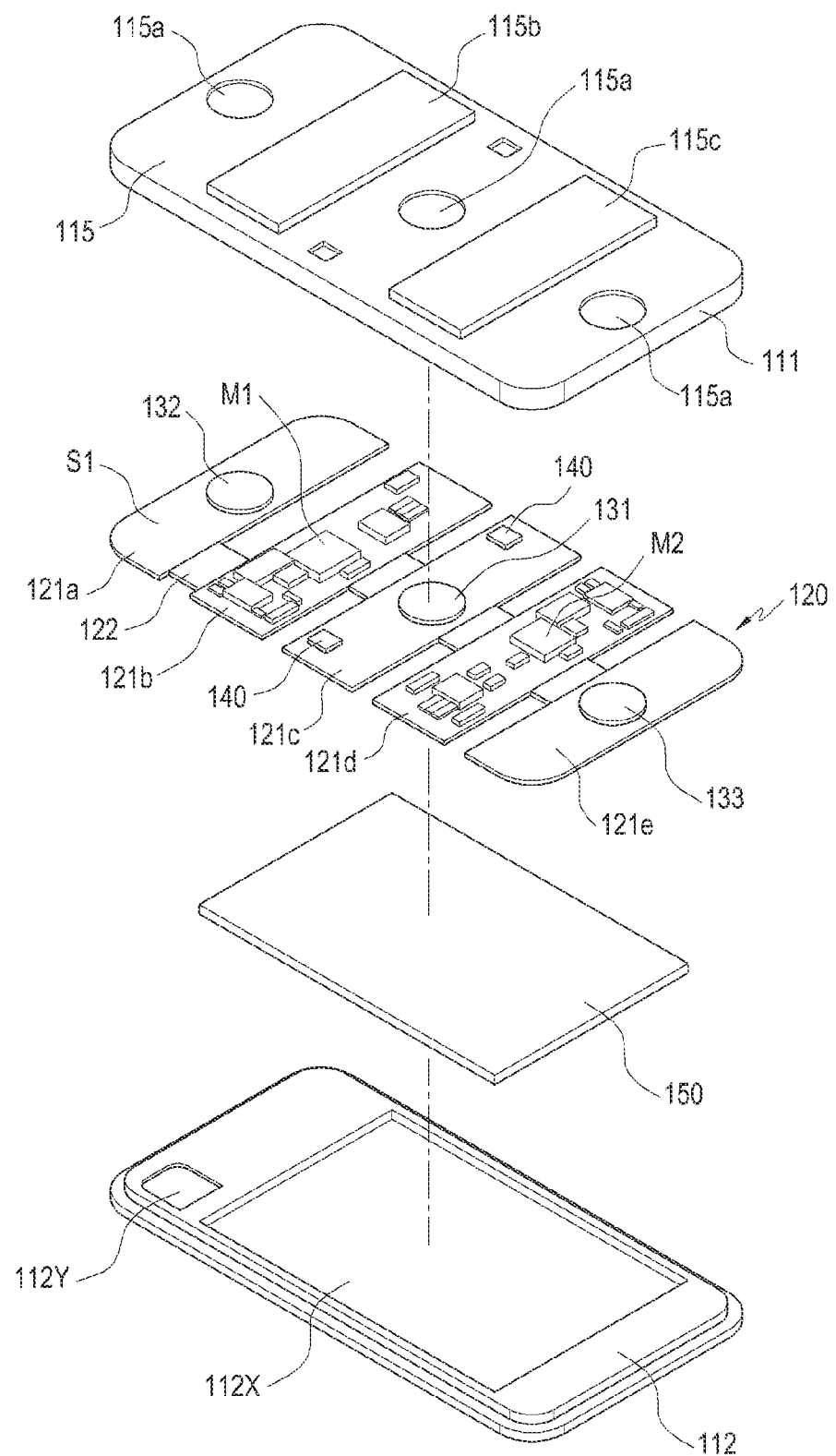
FIG. 2 is a diagram illustrating an exploded perspective view of a wearable biometric information measurement device, according to an embodiment of the present invention.

FIG. 1 is a diagram illustrating a wearable biometric information measurement device, according to an embodiment of the present invention. FIG. 2 is a diagram illustrating an exploded perspective view of the wearable biometric information measurement device, according to an embodiment of the present invention.

Referring to FIGS. 1 and 2, a wearable biometric information measurement device may be defined narrowly or broadly. The wearable biometric information measurement device defined narrowly may refer to devices necessary for only detecting the user biometric information. Namely, the wearable biometric information measurement device of a narrow meaning may refer to a measuring device 100 including a case 110 and a substrate unit 120. Specifically, the biometric information measurement device of a narrow meaning may denote the measuring device 100 that is configured by eliminating a disposable gel pad 200 from the wearable biometric information measurement device of a broad meaning.

On the contrary, the wearable biometric information measurement device 10 defined broadly may refer to all devices capable of measuring the user biometric information. For example, the wearable biometric information measurement device in a broad sense may include the measuring device 100 mentioned above, and the disposable gel pad 200 which is temporarily combined with the measuring device 100. Specifically, the wearable biometric information measurement device may be configured as a combined structure of the measuring device 100 and the disposable gel pad 200. Thus, the user may wear the measuring device 100 combined with the disposable gel pad 200 on his or her body to thereby detect the user biometric information.

As described above, the wearable biometric information measuring device, according to an embodiment of the present invention, may include a measuring device 100 that includes the case 110 and the substrate unit 120. In addition, the measuring device 100 may include an internal battery 150 that supplies power.

The case 110 may be equipped with the substrate unit 120 therein to be sealed. In addition, an attachment surface 115 is provided on one surface of the case 110, to which the disposable gel pad 200 is attached. As will be described in detail below, according to an embodiment of the present invention, elements, such as modules M1 and M2, electrodes 131, 132, and 133, or connection ports 140, are positioned on one surface of the substrate unit 120 (hereinafter, referred to as "the first surface S1"), and the attachment surface 115 is configured to cover the first surface S1. The attachment surface 115 is configured to cover the modules M1 and M2, and to expose electrodes 131, 132, and 133. However, gaps between the attachment surface 115 and the exposed electrodes 131, 132, and 133 or the connection ports 140 may be sealed to prevent the inflow of the impurities.

As described above, the electrodes 131, 132, and 133 or the connection ports 140 mounted on the first surface S1 of the substrate unit 120 are hermetically exposed through the surface of the case 110. The configuration of the case 110 and the electrodes 131, 132, and 133, and the connection ports 140, which are hermetically coupled to each other as one piece, may prevent the inflow of water or sweat to protect elements therein when the user carries the wearable biometric information measurement device or attaches the same to the user's body.

Exposure openings 115a and protrusion surfaces 115b and 115c are formed on the attachment surface 115.

The exposure openings 115a are configured to allow the electrodes 131, 132, and 133 to be hermetically exposed through the surface 115 of the exposure openings 115a. According to the embodiment of the present invention, three electrodes 131, 132, and 133 are illustrated as mounted on the substrate unit 120, so three exposure openings 115a are formed on the attachment surface 115. The inner circumference surfaces of the exposure openings 115a and the outer circumference surfaces of the electrodes may be sealed tightly. Accordingly, since the electrodes 131, 132, and 133, which are exposed through the attachment surface 115, and the exposure openings 115a are coupled in a sealed manner, the inflow of impurities between the same may be prevented. For example, conductive gel members 230 of the disposable gel pad 200 may make contact with the surface of the electrodes 131, 132, and 133. In this case, the inflow of the conductive gel members 230 to the inside of the case 110 through the gaps between the electrodes 131, 132, and 133 and the exposure openings 115a may be prevented.

The protrusion surfaces 115b and 115c are positioned to correspond to the modules M1 and M2. The modules M1 and M2 are arranged between the electrodes 131, 132, and 133 so that the protruding surfaces 115b and 115c are formed adjacent to the exposure openings 115a. In addition, the modules M1 and M2 are mounted on the first surface S1 of the substrate unit 120 to protrude from the same, so the protruding surfaces 115b and 115c are formed to protrude higher than the attachment surface 115 to form module spaces (MS) for the modules M1 and M2. The embodiment of FIGS. 1 and 2 has two modules, i.e., the first module M1, and the second module M2, first protruding surface 115b protrudes from the attachment surface 115 to form a module space (MS) for the first module M1, and second protruding surface 115c protrudes from the attachment surface 115 to form a module space (MS) for the second module M2.

FIGS. 3A to 3E are diagrams illustrating the case that is hermetically coupled, in a wearable biometric information measurement device, according to an embodiment of the present invention.

Figure 3A:
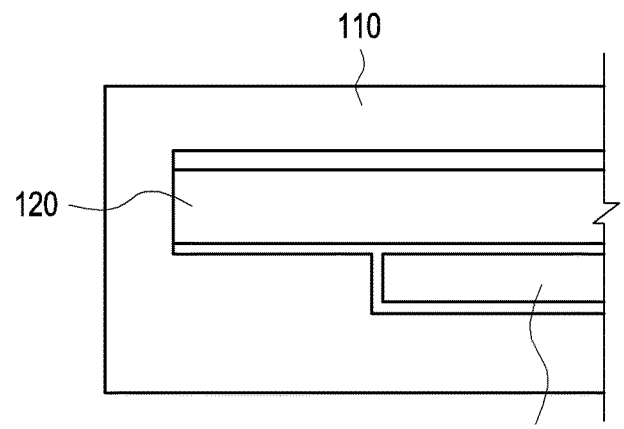
FIGS. 3A to 3E are diagrams illustrating a case that is hermetically coupled in a wearable biometric information measurement device, according to an embodiment of the present invention.

Referring to FIG. 3A, the case 110, according to an embodiment of the present invention, is vacuum-formed as one piece to hermetically enclose the substrate unit 120 therein. That is, the case 110 is vacuum-formed to enclose the substrate unit 120 so that a body 111 and a bottom member 112 are configured as one piece without a connection seam between them. As will be described in greater detail below, the body 111 may be vacuum-formed on the substrate unit 120 to enclose the substrate unit 120, and the bottom member 112 may be vacuum-formed separately. The body 111 and the bottom member 112 may then be fit together. Accordingly, the case 110 may be configured as if it is one piece.

Figure 3B:
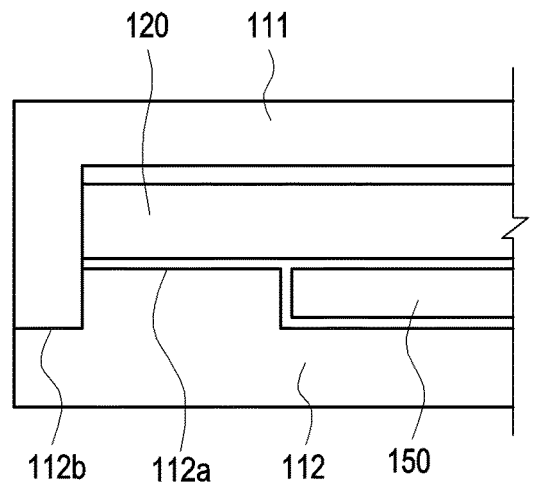
Figure 3C:
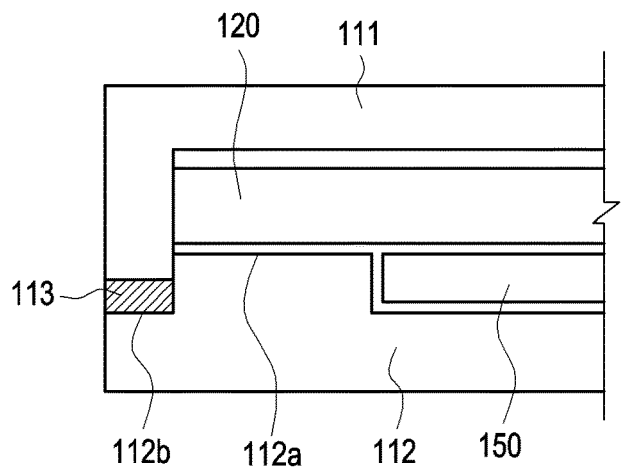

Referring to FIGS. 3B and 3C, as described above, the case 110 includes the body 111 and the bottom member 112, which are hermetically coupled to each other. The body 111 has an attachment surface 115 on one side, and an opposite surface of the attachment surface 115 is open. The body 111 is vacuum-formed on the substrate unit 120 so that the first surface S1 of the substrate unit 120 and the attachment surface 115, i.e., the exposure openings 115a and the electrodes 131, 132, and 133, are configured as sealed, and the modules M1 and M2 are received in the module spaces (see FIG. 7) formed by the protruding surfaces 115b and 115c. The bottom member 112 may be vacuum-formed separately from the body 111, and may be hermetically coupled to the back surface of the body 111. The body 111 and the bottom member 112 may be hermetically coupled to each other by a vacuum-formation.

More specifically, referring to a connection between the bottom member 112 and the body 111, a coupling surface 112b, to which the end of the body 111 is coupled, is provided on the edge of the bottom member 112, and an inner stepped surface 112a, which is higher than the coupling surface 112b, is formed adjacent to the coupling surface 112b. Therefore, when the bottom member 112 is coupled to the body 111, the protruding inner stepped surface 112a of the bottom member 112 makes tight contact with the inner surface of the body 111 to fit on the back of the body 111. Thus, the body 111 and the bottom member 112 may be sealed due to a difference in height between them through a tight coupling. That is, the body 111 and the bottom member 112 may be coupled by the tight contact between the inner stepped surface 112a and the inner surface of the body 111, as well as by a connection of the coupling surface 112b, to thereby prevent the inflow of impurities or water. As described above, the coupling surface 112b may be vacuum-formed on the body 111 to be sealed. In another embodiment, as shown in FIG. 3C, the bottom member 112 and the body 111 may be coupled by the coupling member 113, such as double sided tape, which is interposed between the coupling surface 112b and the body 111.

Figure 3D:
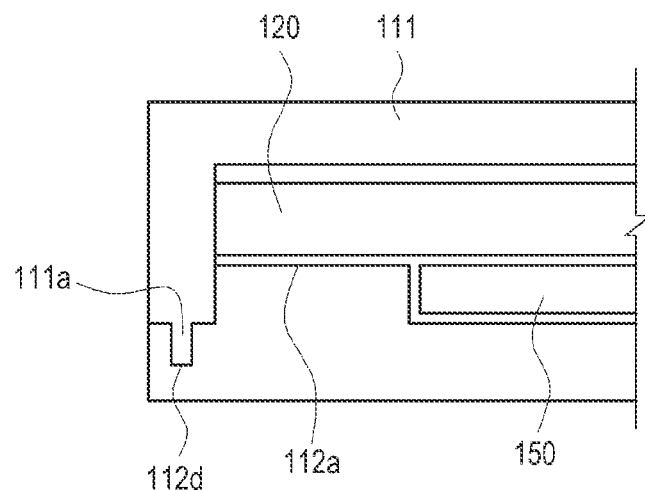
Figure 3E:
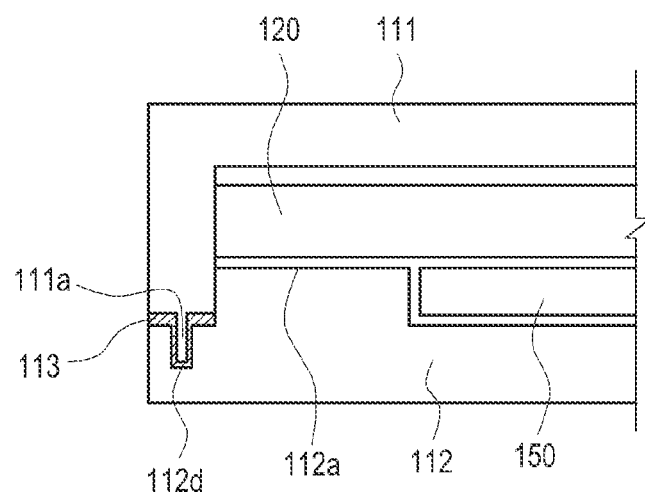

In addition, as shown in FIG. 3D, the configuration of the body 111 and the bottom member 112, which has the coupling surface 112b and the inner stepped surface 112a, further includes a fastening structure provided in the body 111 and the coupling surface 112b. More specifically, the fastening structure includes a protrusion 111a and a fitting groove 112d for hermetically coupling the body 111 and the coupling surface 112b of the bottom member 112. The protrusion 111a may be formed at the edge of the back surface of the body 111, and the fitting groove 112d may be formed on the coupling surface 112b of the bottom member 112 to correspond to the protrusion 111a, so that the protrusion 111a fits into the fitting groove 112d. Therefore, when the body 111 that is vacuum-formed on the substrate unit 120 as one piece is coupled to the bottom member 112 that is separately vacuum-formed, the body 111 rests on the coupling surface 112b, and the protrusion 111a fits into the fitting groove 112d. That is, when the bottom member 112 is coupled to the back surface of the body 111, the protrusion 111a elastically fits into the fitting groove 112d. Thus, the body 111 and the bottom member 112 are sealed by the coupling of the protrusion 111a and the fitting groove 112d, and the contact between the inner stepped surface 112a and the inner surface of the body 111, as well as the coupling surface 112b. In addition, as shown in FIG. 3E, the coupling member 113, such as a double-sided tape, may be interposed between the coupling surface 112b and the body 111. The coupling member 113 may enhance the sealing reliability. In addition, although the protrusion 111a is provided on the body 111, and the fitting groove 112d is provided on the bottom member 112 in the present embodiment, they may be configured in reverse. For example, the protrusion 111a may be provided on the bottom member 112, and the fitting groove 112d may be on the body 111. Although various examples for coupling the case 110 are described above, a structure and a coupling method of the case 110 are not limited thereto, and the coupling structure or the shape of the case may be modified or altered as long as the case can enclose the substrate unit 120 and can provide a waterproof function. The bottom member 112 may have an accepting recess 112X and a switch-accepting recess 112Y, which are formed thereon. The accepting recess 112X may accept the internal battery 150 provided on the back of the substrate unit 120, and the switch-accepting recess 112Y may accept a switching unit 125 provided on the back of the substrate unit 120, as described in greater detail below.

The case 110 may be made of an elastic material, which provides a sealing function, such as, for example, a rubber-based material, an urethane-based material, or an elastomer-based material, which are elastic and enable the case 110 to be flexible according to the movement of the user while it is attached to the user's body. In addition, the case 110 may be made of a non-conductive material, or an insulating material, for example, an insulating resin. In addition, the case 110, according to an embodiment of the present invention, may have various shapes, including a rectangle, according to the connection status of substrates 121a, 121b, 121c, 121d, and 121e of the substrate unit 120.

Figure 4A:
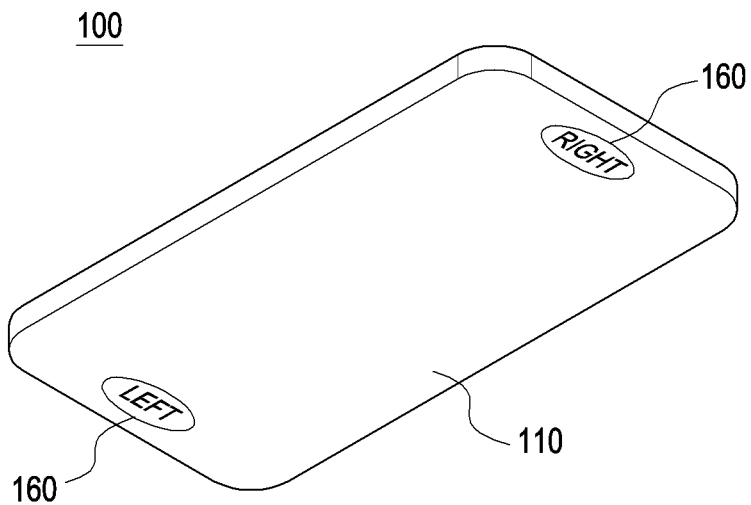
FIGS. 4A and 4B are diagrams illustrating a marked point on the surface of a case in a wearable biometric information measurement device, according to an embodiment of the present invention.
Figure 4B:
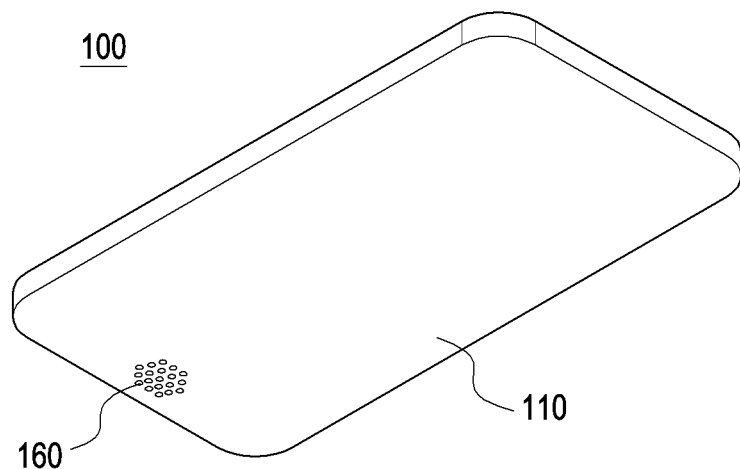

FIGS. 4A and 4B are diagrams illustrating a marked point on the surface of the case in a wearable biometric information measurement device, according to an embodiment of the present invention.

Referring to FIGS. 4A and 4B, a marked point 160 is provided on the surface of the case 110 to show an attachment reference point so that the user identifies a direction and a position of the measuring device 100 that is to be attached to the user's body. For example, the electrodes 131, 132, and 133 may be disposed, with the modules M1 and M2 interposed between them, on the substrate unit 120, according to an embodiment of the present invention. The user biometric information, such as an ECG, may be detected through a potential difference between centered electrode 131 as a reference electrode, and the electrodes 132 and 133 on both sides thereof. In attaching the measuring device 100 to the user's body part close to the heart for measuring an ECG, if the measuring device 100 is attached in a reversed direction, an ECG data graph may be displayed in reverse, compared with a normal measurement graph. Although the user can recognize incorrect attachment of the measuring device through the reversed display of the biometric information, such as ECG data, the marked point 160 can inform the user of the attachment direction of the measuring device 100 in advance. Furthermore, repeated incorrect attachment of the measuring device 100 may lower the adhesive strength of an attachment member with respect to the user's body. As described in greater detail below, the attachment force of a pad member, which is to be attached to the user's body, may be different according to adhesive materials thereof when it is reused. Also, as described in greater detail below, a silicon-based adhesive or an urethane-based adhesive may be used as the material of the pad member, according to an embodiment of the present invention. In this case, the attachment force of the urethane-based adhesive may be considerably lowered when it is reused, whereas the attachment force of the silicon-based adhesive may remain even when it is reused, so it can be used repeatedly. However, there may be a difference in the price between the silicon-based adhesive and the urethane-based adhesive.

The marked point 160, according to an embodiment of the present invention, is printed on the surface of the case 110, as shown in FIG. 4A, or is provided in the form of a plurality of protrusions, as shown in FIG. 4B to indicate its position, but the present disclosure is not limited thereto. Any configuration, which can inform the user of the correct attachment status of the biometric information measurement device 10, when it is attached to the user's body, may be applied to the present invention.

Figure 5:
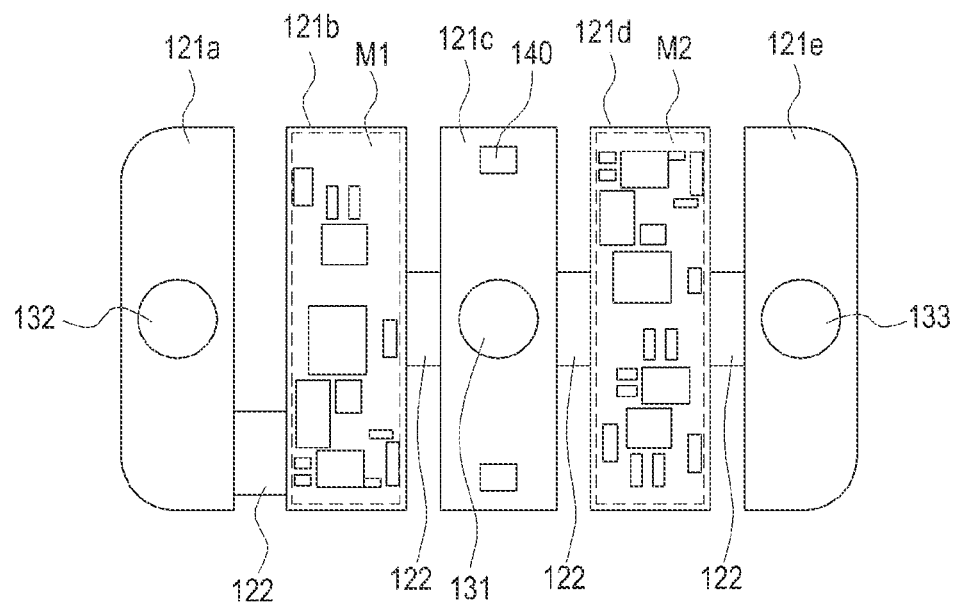
FIG. 5 is a diagram illustrating a first surface of a substrate unit in a wearable biometric information measurement device, according to an embodiment of the present invention.
Figure 6:
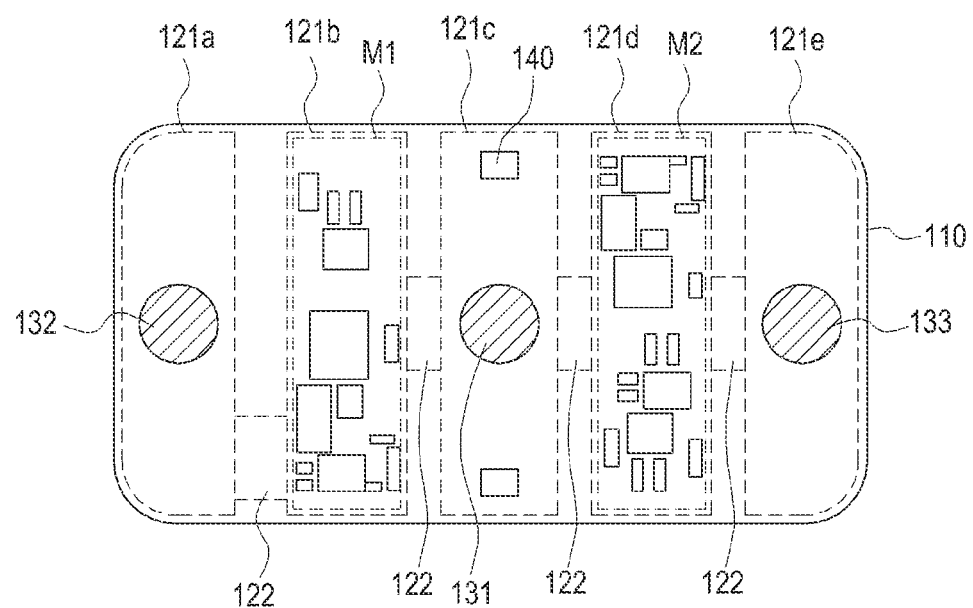
FIG. 6 is a diagram illustrating a wearable biometric information measurement device in a coupled state, according to an embodiment of the present invention.

FIG. 5 is a diagram illustrating a first surface of the substrate unit in the wearable biometric information measurement device, according to an embodiment of the present invention. FIG. 6 is a diagram illustrating a back surface of the substrate unit 120 in the wearable biometric information measurement device, according to an embodiment of the present invention.

Referring to FIGS. 5 and 6, the substrate unit 120 is enclosed in the case 110. The substrate unit 120 has the first surface S1 on which biometric information measurement members A (referred to as "biometric information measurement modules A," see FIG. 9), such as the modules M1 and M2, and the electrodes 131, 132, and 133, or connection ports 140 are mounted, and the opposite surface of the first surface S1. The first surface S1 faces the attachment surface 115, and faces the user's body when the measuring device 100 is attached to the user's body.

The substrate unit 120, according to an embodiment of the present invention, includes the substrates 121a, 121b, 121c, 121d, and 121e, and flexible circuit boards 122 electrically connecting the substrates.

The substrates 121a, 121b, 121c, 121d, and 121e are disposed adjacent to each other so that the modules M1 and M2, and the electrodes 131, 132, and 133 are arranged to alternate with each other. In addition, the substrates 121a, 121b, 121c, 121d, and 121e are electrically connected with each other through the flexible circuit boards 122 interposed between them. It is assumed that the first substrate 121a is in the leftmost position, and the second to the fifth substrates 121b, 121c, 121d, and 121e are arranged from the first substrate 121a to the right in sequence, in FIG. 5.

As described above, the biometric information measurement modules A, such as the modules M1 and M2, and the electrodes 131, 132, and 133, or elements, such as the connection ports 140 may be mounted on the first surface S1 of the substrate unit 120. Particularly, according to an embodiment of the present invention, the modules M1 and M2, and the electrodes 131, 132, and 133 may be arranged to alternate with each other on the first surface S1 of the substrate unit 120 The first to the third electrodes 131, 132, and 133 may be positioned at the center and at both ends of the substrate unit 120, respectively, and the modules M1 and M2 may be positioned between the same. Accordingly, first electrode 131 is mounted on the first surface S1 of the third substrate 121c at the center of the substrate unit. Second electrode 132 is mounted on the first surface S1 of the first substrate 121a. Third electrode 133 is mounted on the first surface S1 of the fifth substrate 121e. That is, the second electrode 132, the first electrode 131, and the third electrode 133 are mounted on the first substrate 121a, the third substrate 121c, and the fifth substrate 121e, respectively. In addition, first module M1 is mounted between electrodes, i.e., on the second substrate 121b between the first substrate 121a having the second electrode 132 thereon and the third substrate 121c having the first electrode 131 thereon. The second module M2 is mounted between electrodes, i.e., on the fourth substrate 121d between the third substrate 121c having the first electrode 131 thereon and the fifth substrate 121e having the third electrode 133 thereon.

Although this embodiment of the present invention describes three electrodes (hereinafter, referred to as "three channels") that detect the biometric information signals, the present invention is not limited thereto. For example, two electrodes (hereinafter, referred to as "two channels") may detect the biometric information signals.

As described above, the modules M1 and M2, and the electrodes 131, 132, and 133 are mounted on the first surface S1 of the substrate unit 120, and the connection ports 140 that are electrically connected with external ports are mounted on the same. As will be described in greater detail below, perception sensors 190 for detecting the attachment of the disposable gel pad 200 may also be provided (see FIG. 16). The connection ports 140 may be exposed hermetically through the attachment surface 115 to be thereby electrically connected with an external device. Since the connection ports 140 are provided on the first substrate S1, they may not be contaminated except for when they are connected with the external device. More specifically, when the user attaches the measuring device 100 to his or her body, a disposable gel pad 200 may be attached to the attachment surface 115. Accordingly, the attachment surface 115 is not exposed to the outside because the disposable gel pad 200 is attached onto the same, and the connection ports 140 are attached to one side of the disposable gel pad 200 not to be exposed to the outside. For example, even when the user takes a shower while the measuring device 100 is attached to the user's body, the connection ports 140 may be covered by the disposable gel pad 200 and are not exposed to the outside. The connection ports 140, according to an embodiment of the present invention, may be configured as a charging connection ports 140 for charging the internal battery 150, which will be described in greater detail below. However, the connection ports 140 are not limited to the charging connection ports 140, and may be modified and altered. For example, the connection ports 140 may be connected with ports of the external device to perform data pairing of the measuring device 100 with the external device, or vice versa.

Figure 7:
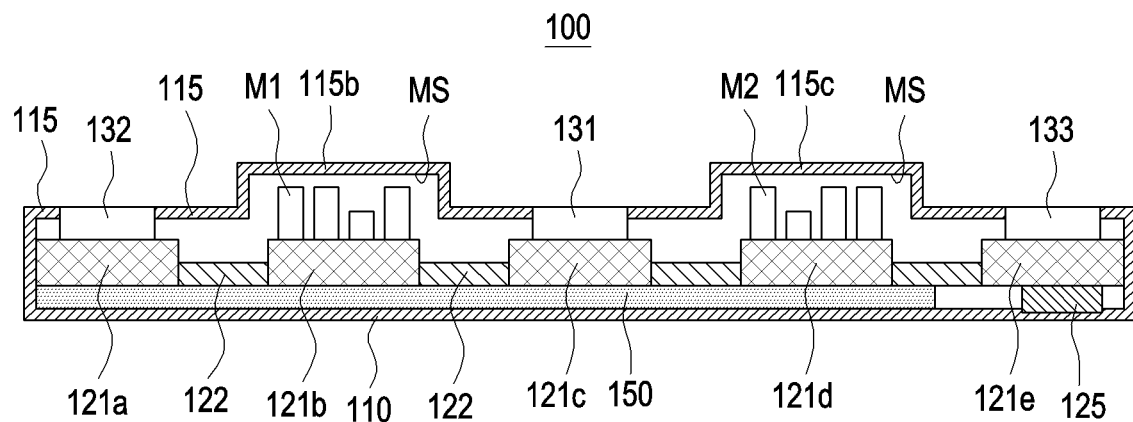
FIG. 7 is a diagram illustrating a cross-section a measuring device in a wearable biometric information measurement device, according to an embodiment of the present invention.
Figure 8:
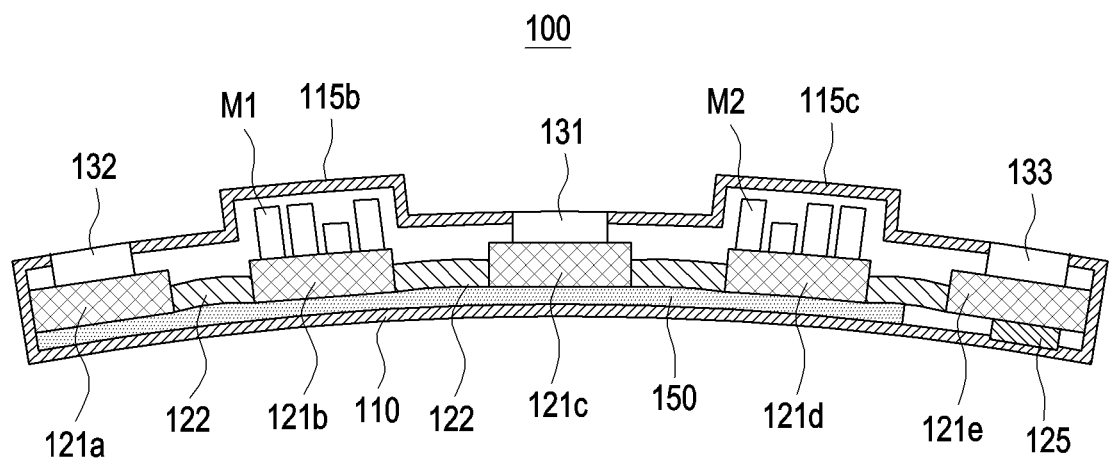
FIG. 8 is a diagram illustrating a cross-section of a measuring device that has been bent, in a wearable biometric information measurement device, according to an embodiment of the present invention.

FIG. 7 is a diagram illustrating a cross-section of a measuring device in a wearable biometric information measurement device, according to an embodiment of the present invention. FIG. 8 is a diagram illustrating a cross-section of a measuring device that has been bent, in a wearable biometric information measurement device, according to an embodiment of the present invention.

Referring to FIGS. 7 and 8, the flexible circuit boards 122 are provided between the substrates 121a, 121b, 121c, 121d, and 121e, more specifically, between the first substrate 121a and the second substrate 121b, between the second substrate 121b and the third substrate 121c, between the third substrate 121c and the fourth substrate 121d, and between the fourth substrate 121d and the fifth substrate 121e. The flexible circuit boards 122 allow the substrates 121a, 121b, 121c, 121d, and 121e to be bent or transformed with electrical connections between them. If the substrate unit 120, according to an embodiment of the present invention, is configured as the hard body 111, it is difficult to bend or transform the hard substrate unit according to the curvature of the body or the movement of the user while it is attached to the user's body. In an embodiment of the present invention, the plurality of hard substrates 121a, 121b, 121c, 121d, and 121e are connected through the flexible circuit boards 122 so that the substrates 121a, 121b, 121c, 121d, and 121e can be easily bent or transformed. Therefore, the measuring device 100 may be attached to curved body parts, and may be transformed according to the movement of the user. Thus, the reliability of attachment of the wearable biometric information measurement device 10 can be enhanced, and user convenience in activities while wearing the wearable biometric information measurement device can be maximized. Although the measuring device 100 is shown to be convexly bent in the present embodiment, it is not limited thereto. For example, the measuring device 100 may be concavely bent, and it is obvious that the measuring device 100 may be bent in various forms according to the movement of the user while wearing the same.

Since the electrodes 131, 132, and 133, and the modules M1 and M2 are mounted on the same side, i.e., the first surface S1 of the substrate unit 120, according to an embodiment of the present invention, the size and thickness of the wearable biometric information measurement device may be decreased. Particularly, the measuring device 100 (i.e., the case 110) has a horizontal (X-axial) length of 50~70 mm, a vertical (Y-axial) length of 18~30 mm, and a (Z-axial) thickness of 2.5~3.7 mm, and even though the disposable gel pad 200 is coupled to the measuring device 100, there is no difference in the (Z-axial) thickness, which still remains in the range of 2.5~3.7 mm. Therefore, the user can conveniently carry the measuring device, and if necessary, the user may attach the measuring device to his or her body to measure and record the user's health information (see FIG. 1).

As described above, the electrodes 131, 132, and 133 mounted on the first surface S1 of the substrate unit 120 may be exposed through the attachment surface 115, and the modules M1 and M2 may be accepted in the module spaces (MS) inside the first and the second protruding surfaces 115b and 115c.

According to an embodiment of the present invention, three or more electrodes 131, 132, and 133 may be adopted. For example, in order to measure an ECG, a reference electrode {a right-leg (RL) electrode}, a right-arm (RA) electrode, and a left-arm (LA) electrode may be provided. The first electrode 131 may be configured as the reference electrode, and the second electrode 132 and the third electrode 133 may be configured as detection electrodes, i.e., the RA electrode and the LA electrode, which are provided on both sides of the reference electrode to detect a potential difference. As set forth above, the electrodes 131, 132, and 133, according to an embodiment of the present invention, may measure the biometric signal generated by a physiological potential difference of the body. In addition, the electrodes 131, 132, and 133, according to an embodiment of the present invention, may measure an electromyogram (EMG), an electroencephalogram (EEG), a galvanic skin reflex (GSR), and an electrooculography (EOG), as well as an ECG.

The modules M1 and M2 mounted on the first surface S1 of the substrate unit 120 may include a transmitting/receiving module, an analog front-end processing module, a controller 170, one or more detecting modules (hereinafter, referred to as "detecting sensors"), and a memory module. In the this embodiment of the present invention, the first module M1 on the first surface S1 of the second substrate 121b includes the transmitting/receiving module, and the second module M2 on the first surface S1 of the fourth substrate 121d includes the analog front-end processing module, the controller 170, the detecting sensors, or the memory module. However, the mounting position and the arrangement of the modules M1 and M2 may be modified or changed in various ways.

Figure 9:
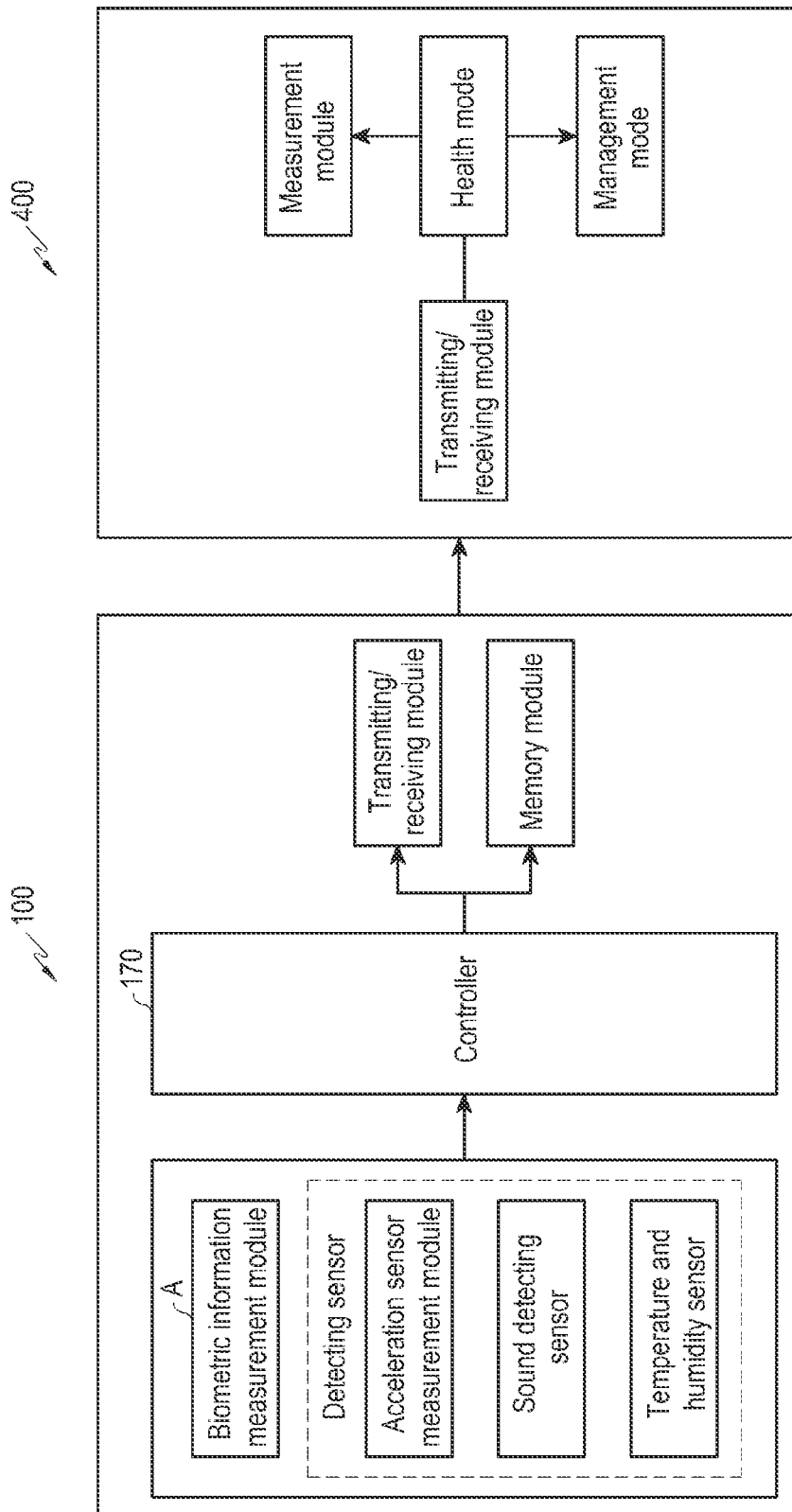
FIG. 9 is a block diagram illustrating a wearable biometric information measurement device, according to an embodiment of the present invention.

FIG. 9 is a block diagram illustrating a wearable biometric information measurement device, according to an embodiment of the present invention.

FIG. 9 shows the configuration of the modules M1 and M2 among the biometric information measurement modules "A" including the electrodes 131 and 132, or the modules M1 and M2. First, the analog front-end processing module in the configuration of the modules M1 and M2 may be positioned on the first surface S1 of the fourth substrate 121d. The analog front-end processing module may process ECG signals from the user, which are measured through the electrodes 131, 132, and 133. That is, when the analog biometric signals are detected through the electrode 131, 132, and 133, the analog front-end processing module may convert the biometric signal into digital biometric signal data.

The analog front-end processing module may include an analog signal processing unit, an analog/digital (A/D) converter, a digital signal processing unit, or the like. The analog signal processing unit may include an amplifier that amplifies weak signals of the body, which are detected by the electrodes 131, 132, and 133, and a filter that eliminates noise resulting from the biometric signal measurement. The A/D converter may convert analog biometric signals transmitted from the analog signal processing unit into digital biometric signal data. The digital signal processing unit may process the digital biometric signal data received from the A/D converter through a specific digital calculating operation (e.g., fast Fourier transform (FFF) calculation, differential calculation, or averaging calculation).

The detecting sensors, according to an embodiment of the present invention, may be mounted on the first surface S1 of the fourth substrate 121d to be adjacent to the analog signal processing unit. The detecting sensor may be configured to detect user activities or various user states. A single user environment may be detected by a single detecting sensor, and a plurality of user environments may be detected by a plurality of detecting sensors. The plurality of detecting sensors may detect different user status information values (e.g., a biometric signal detection value, an acceleration sensor detection value, or a temperature/humidity sensor detection value according to the movement of the user). The detection values may be combined to create user status information. For example, if the heart rate has been increased, and furthermore, if the acceleration sensor has detected a signal of fast walking (running) from the user, the increase in the heart rate may be determined to stem from the user exercise.

The detecting sensor, according to an embodiment of the present disclosure, may be at least one of an acceleration sensor, a humidity sensor, a temperature sensor, or a sound detecting sensor, or a combination thereof. For example, the acceleration sensor, i.e., a three-axis acceleration sensor, may detect X-axis, Y-axis, and Z-axis data of the user according to the user activities, and may measure a change in the user posture due to physical activities, such as, for example, walking, running, the number of steps, fainting, falling, tripping, or the like, through the measured values. The measured data may help in preventing diseases related to the user's lifestyle, for example, metabolic syndrome, diabetes, high blood pressure, hyperlipidemia, or the like.

The temperature sensor may detect the body temperature of the user or the temperature of an external environment, and may determine a change in the body temperature, and the environment of the user through the detected values.

The humidity sensor may detect the humidity of an environment, or the user status through sweat of the user, and may identify the user activities, such as, for example, exercising, hot-bathing, taking a shower, or the like, through the detected values.

In addition, the sound detecting sensor may detect sounds, for example, eating-sounds, from the user, or external sounds. For example, people with diabetes need to frequently check blood sugar that is different before and after eating. Thus, in the case of adopting the sound detecting sensor, it can be recognized whether a blood sugar value has been measured before or after eating in addition to the monitoring of the blood pressure. In addition, in the case of people having an irregular heartbeat, the heart rate and the blood pressure tend to increase during eating. Therefore, it can be checked whether data of the heart rate or the blood pressure has been measured before or after eating.

As described above, various detecting sensors or a plurality of detecting sensors may be adopted. The data values detected by the sensors may be combined together to measure the user status. For example, when adopting the acceleration sensor and the temperature/humidity sensor, the acceleration sensor may detect the user status related to the user's posture or movement, and the temperature/humidity sensor may detect a change in the body temperature of the user, a change in humidity, such as a sweat of the user, or the temperature and the humidity of the environment. According to the detected values of the acceleration sensor and temperature/humidity sensor, a change in the biometric signals may be detected. For example, when the user exercises, the acceleration sensor and the temperature/humidity sensor may detect a change in the user's body so that a change in the biometric signals may be detected as well. The user status, such as the biometric signal change during exercise, may be determined by a combination of the detected values, which provides more accurate detection data according to the movement of the user.

In addition, the user status or the health status may be detected by a combination of the detected values and the biometric signal values as well as by a combination of the detected values of the detecting sensors. For example, the heart rate and the blood pressure of people having an irregular heartbeat tend to increase during eating, as set forth above. When adopting the sound detecting sensor, a value detected by the sound detecting sensor, which detects the eating sound, and a signal value detected by the biometric information member are combined to thereby obtain the accurate data on the user status, which shows that the increase in the heart rate and the blood pressure of the irregular heartbeat patient has been caused by the eating.

The user status, such as physical activities of the user, may be converted into data through the biometric signal detecting values measured by the biometric information measurement module "A" and the detected values of the detecting sensors to thereby analyze the biometric signal change according to the physical activities of the user. In addition, the biometric signals may be analyzed based on the user status, such as the physical activities, through the detected values of the detecting sensors to thereby provide a healthcare service that is more accurate and suitable for the user.

Here, "user status" includes body information, such as the user's posture, physical activity information, external environment information, or the like. That is, the user status encompasses the user's lifestyle and life environment.

The memory module may store and manage the biometric signal data and the user status information data obtained through the electrodes 131, 132, and 133, or the detecting module. The memory module may be a RAM and/or a flash memory.

The transmitting/receiving module may be configured to share the detected value data with a separate electronic device 400. The transmitting/receiving module may include at least one of a Bluetooth module, a near field communication (NFC) module, or a WiFi module to thereby make a data pairing with the external electronic device 400. In addition, the transmitting/receiving module may transmit data to the external electronic device 400 through a short-range communication devices, such as an radio frequency (RF) system, a wireless local area network (WLAN), or zigbee. That is, the measuring device 100 may share the health information monitoring result of the user (an ECG, a stress index, a breathing rate per minute, which are measured by the ECG sensor, or a sleep pattern and the number of steps, which are measured by the accelerated sensor) with the electronic device 400, such as smart phones, through the transmitting/receiving module, so that the user can measure and check his or her health information anytime and anywhere.

Figures 31, 32:
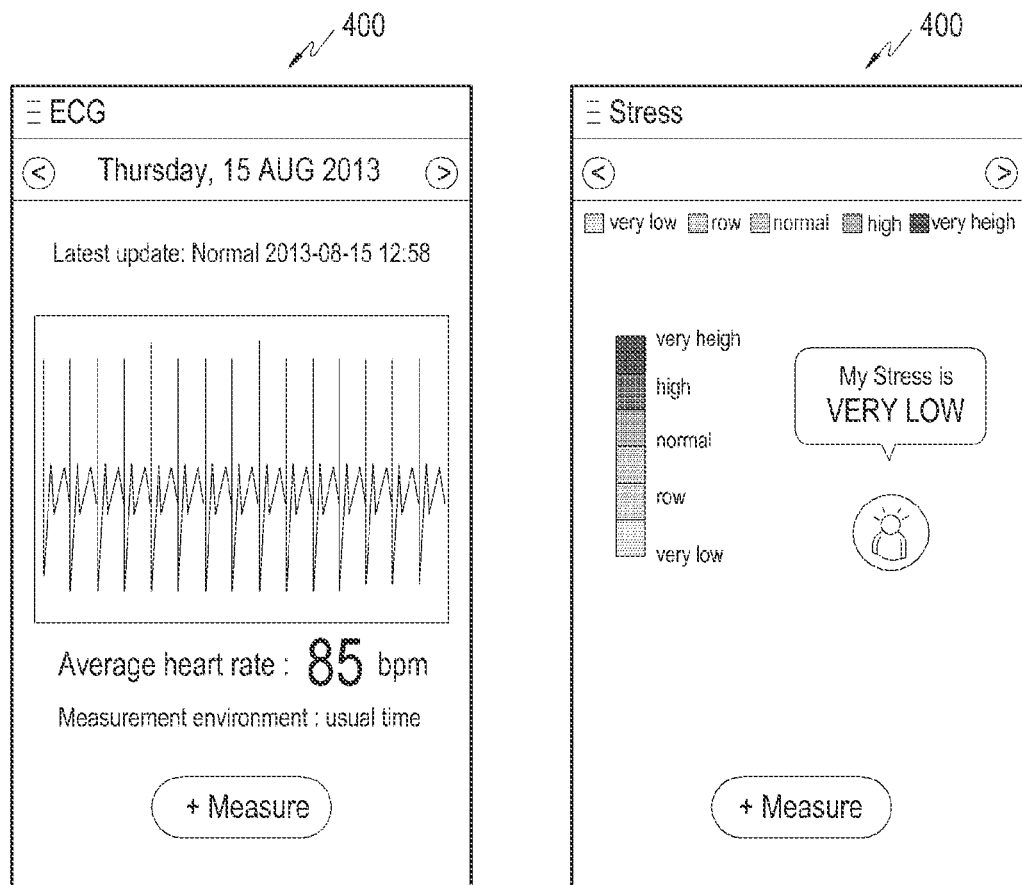
FIG. 31 is a diagram illustrating the display of ECG signal information detected through a wearable biometric information measurement device on an external electronic device, according to an embodiment of the present invention.
FIG. 32 is a diagram illustrating the display of a user stress index on an external electronic device through signal information detected by a wearable biometric information measurement device, according to an embodiment of the present invention.

A controller 170 may receive the biometric information signals detected by the electrodes 131, 132, and 133, or the detected values of the detecting modules to store the biometric information data and the user status information data in the memory module, or may control the transmitting/receiving module to transmit and receive the data to and from the separate electronic device 400 (see FIG. 31).

In addition, the controller 170 may create individual user ID profiles (hereinafter, referred to as "individual user profiles"), based on the received biometric information signals or the user status information, or to store and manage the data that has been measured and analyzed in the measuring device 100 using the created individual user profile.

Figure 10:
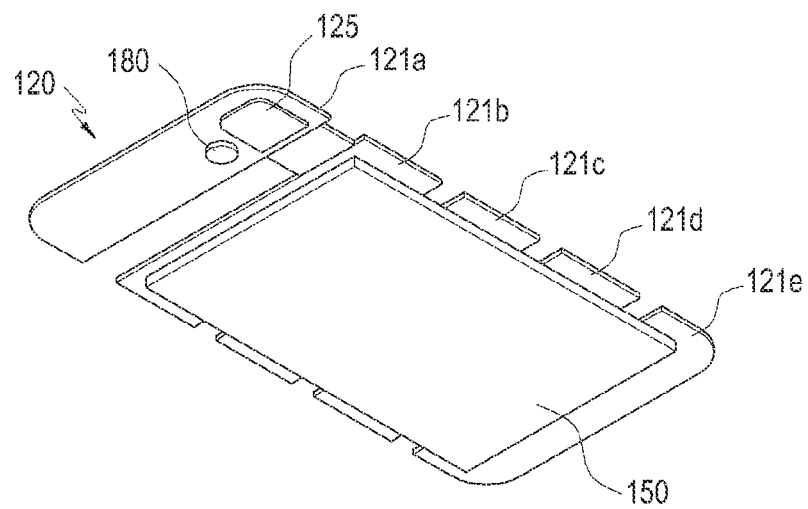
FIG. 10 is a diagram illustrating a configuration in which an internal battery is provided on a back surface of a first surface of a substrate unit in a wearable biometric information measurement device, according to an embodiment of the present invention.
Figure 11:
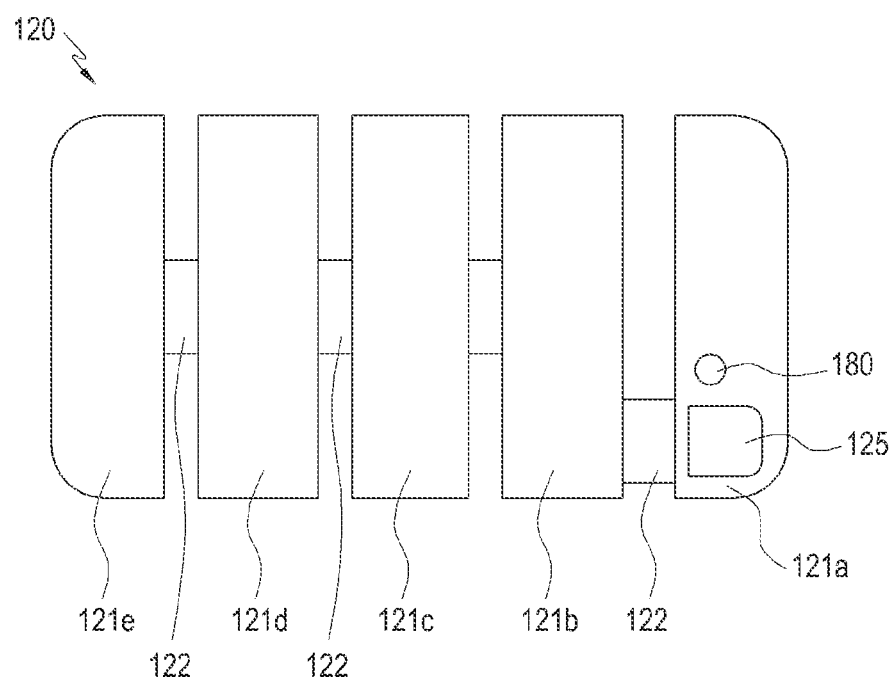
FIG. 11 is a diagram illustrating an opposite surface of the first surface of the substrate unit in the wearable biometric information measurement device, according to an embodiment of the present invention.

FIG. 10 is a diagram illustrating a configuration in which the internal battery is provided on the opposite surface of the substrate unit in the wearable biometric information measurement device, according to an embodiment of the present invention. FIG. 11 is a diagram illustrating the opposite surface of the substrate unit in the wearable biometric information measurement device, according to an embodiment of the present invention.

Referring to FIGS. 10 and 11, the opposite surface of the first surface S1 of the substrate unit 120 (hereinafter, referred to as a back surface of the substrate unit 120) may be provided with the internal battery 150 for supplying power to the biometric information measurement modules "A", a switching unit 125 for turning on/off the measuring device 100, and a notification unit 180 for indicating the charging status of the internal battery 150 and the on/off state of the switching unit 125, or informing of malfunction of the measuring device 100.

The internal battery may be mounted on the back surface of the substrate unit 120 to be enclosed inside the case 110 together with the substrate unit 120, and may be a rechargeable battery. In addition, the internal battery is electrically connected with the switching unit 125, as described in greater detail below, so that the supply of power from the internal battery 150 to the biometric information measure modules may be controlled according to the manipulation of the switching unit 125. As described above, the connection ports 140 may be provided in the first surface S1 of the substrate unit 120 to be connected with a charging module 300 to charge the internal battery 150. The connection port 140 makes a contact with a connection pin 340 of the charging module 300 to charge the internal battery 150, as will be described in greater detail below.

The switching unit 125 turns the measuring device 100 on or off. The switching unit 125, according to an embodiment of the present invention, may be configured as mechanical buttons.

The notification unit 180 may be provided on the back surface of the substrate unit 120, and may indicate the charging status or the remaining power of the internal battery 150 when charging the internal battery 150, or inform of a malfunction of the measuring device 100. The notification unit 180 may inform the user of the information by at least one of a visual method, an acoustic method, or a tactile method. For example, the notification unit may be configured as an optical module, such as light emitting diodes (LEDs), an acoustic module for emitting a sound through a speaker, or a vibrating module for generating vibration such as, for example, haptics. Although the notification unit 180 is configured as at least one of the optical module, the acoustic module, or the vibrating module in this embodiment, the present invention is not limited thereto, and the notification unit 180 may be modified and changed in various ways. For example, the optical module may be provided together with the acoustic module, or the optical module and the vibrating module may be provided together.

The notification unit 180 is provided in the wearable biometric information measurement device 10 to inform of the status thereof. However, the notification unit 180 may be provided as a notification module to allow the external electronic device 400 to display the status of the wearable biometric information measurement device 10, e.g., the charging status or the remaining power of the internal battery, or a malfunction of the measuring device.

Figure 12:
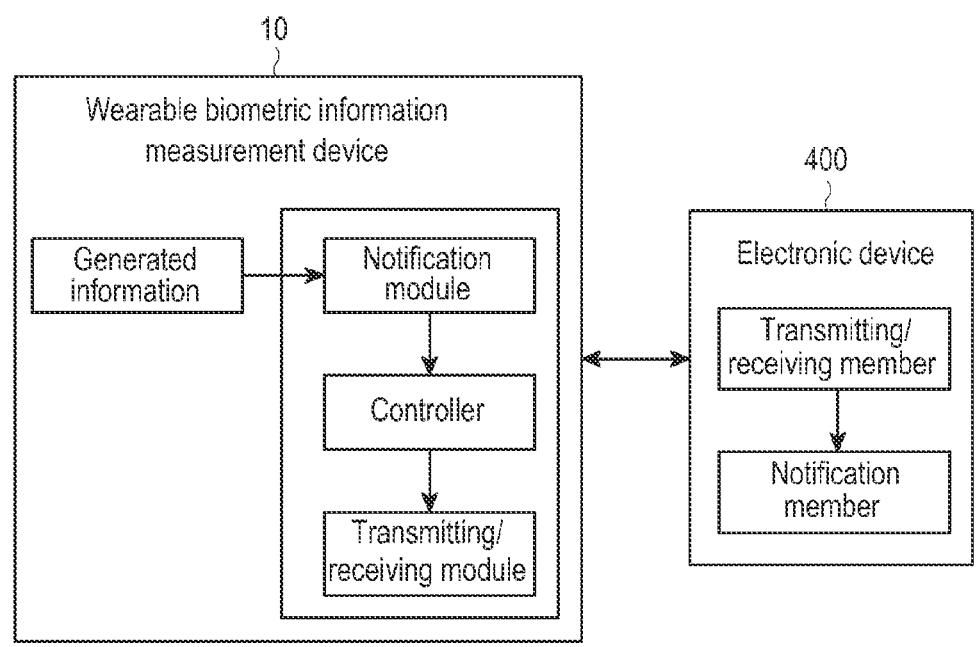
FIG. 12 is a diagram illustrating a notification unit in a wearable biometric information measurement device, according to an embodiment of the present invention.

FIG. 12 is a diagram illustrating a notification unit in a wearable biometric information measurement device, according to an embodiment of the present invention.

Referring to FIG. 12, the notification unit 180, as described above, may be recognized by the user through the measuring device 100, whereas the notification unit 180, according to this embodiment, may be configured to inform of the status of the measuring device 100 through the separate electronic device 400 that interworks with the measuring device 100. That is, the information signals for the driving of the measuring device 100, the charging status of the internal battery 150, or malfunction of the measuring device 100 may be applied to the notification module 180 according to the on/off-state of the switching unit 125. The signal applied to the notification module 180 is transferred to the controller 170, and the controller may control the transmitting/receiving module to transmit the information to the electronic device 400. The electronic device 400 that has received the information may display the information on the screen, and may further drive the notification means, such as a vibration and a sound to thereby allow the user to recognize the same.

Figure 13:
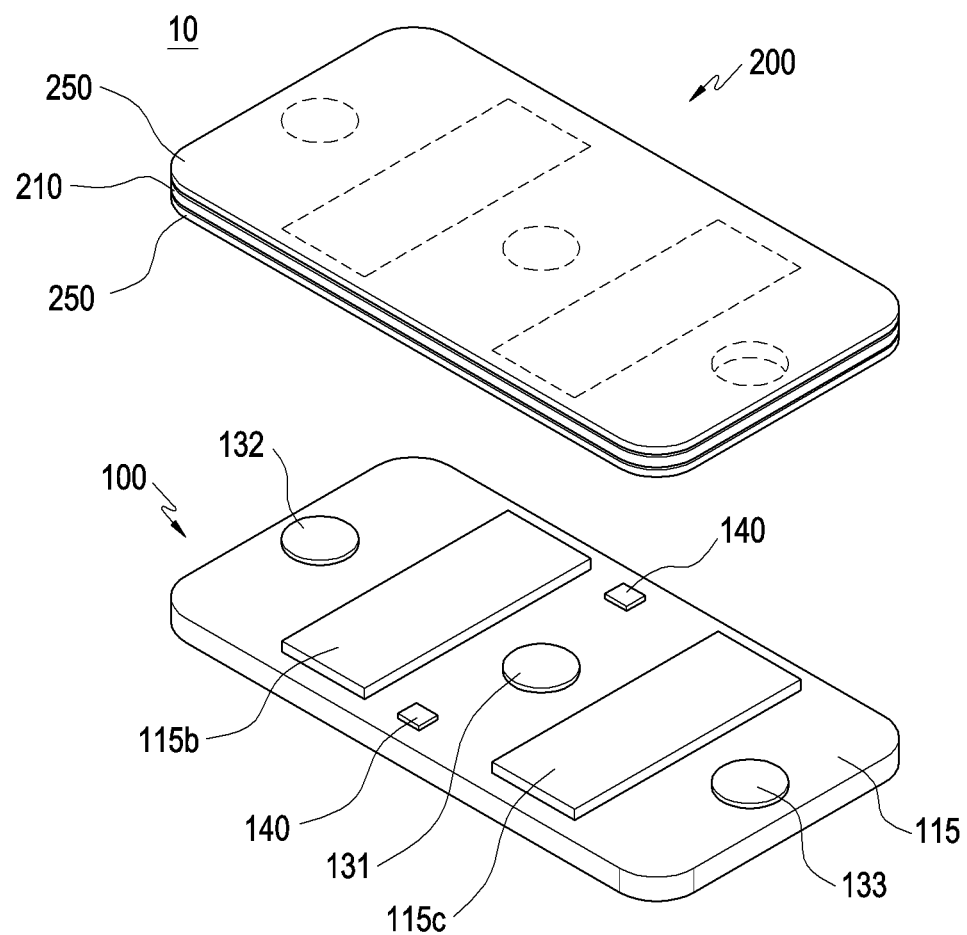
FIG. 13 is a diagram illustrating a measuring device and a disposable gel pad that is to be attached to the measuring device in a wearable biometric information measurement device, according to an embodiment of the present invention.
Figure 14:
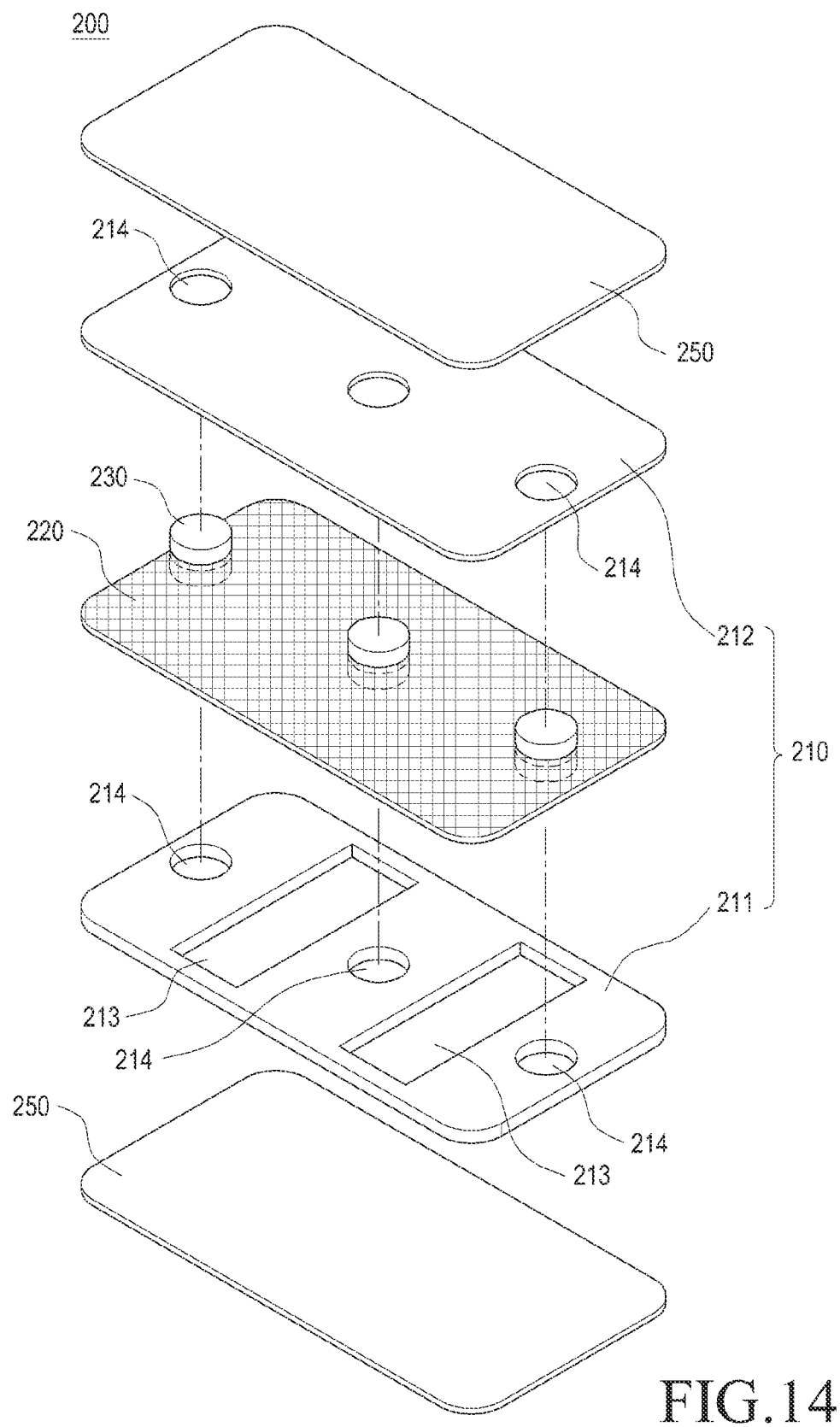
FIG. 14 is a diagram illustrating an exploded perspective view of a disposable gel pad in a wearable biometric information measurement device, according to an embodiment of the present invention.

FIG. 13 is a diagram illustrating a measuring device and disposable gel pad that is to be attached to the measuring device, in a wearable biometric information measurement device, according to an embodiment of the present invention. FIG. 14 is a diagram illustrating an exploded perspective view of the disposable gel pad, in a wearable biometric information measurement device, according to an embodiment of the present invention.

Referring to FIGS. 13 and 14, a disposable gel pad 200 includes a pad member 210 and conductive gel members 230. In addition, the disposable gel pad 200 may further include a mesh member 220 and film covers 250.

Both surfaces of the pad member 210 are provided with an adhesive to be attached to the attachment surface 115 and the body, respectively. The pad member 210 has receiving openings 213 and through openings 214.

The receiving openings 213 may receive the first and the second protruding surfaces 115b and 115c when the disposable gel pad 200 is attached to the attachment surface 115, and the receiving openings 213 have a similar size to the first and the second protruding surfaces 115b and 115c to allow the first and the second protruding surfaces 115b and 115c to be inserted into the receiving openings 213. The receiving openings 213, according to an embodiment of the present invention, may be shaped into rectangles to correspond to the shape of the first and the second protruding surfaces 115b and 115c. However, the receiving openings 213 may be variously modified and changed in shape.

As will be described in greater detail below, the pad member 210 includes the first pad portion 211 and the second pad portion 212, and the receiving openings 213 are provided in the first pad portion 211. That is, the first pad portion 211 has the receiving openings 213 that are formed through the first pad portion 211 at the positions corresponding to the first protruding surface 115b and the second protruding surface 115c, and the second pad portion 212 is configured to cover the receiving openings 213. The through openings 214 may be formed as holes penetrating through the pad member 210 so that the through openings 214 can be connected with the electrodes 131, 132, and 133 when the disposable gel pad 200 is attached to the attachment surface 115. In order to allow the electrodes 131, 132, and 133, and the disposable gel pad 200 to make contact with the user's body, the through openings 214 may be formed in both the first pad portion 211 and the second pad portion 212. That is, the first pad portion 211 and the second pad portion 212 may be combined into a single pad member 210 so that the through openings 214 penetrate both sides of the pad member 210.

The first pad portion 211 may have a specific thickness. Adhesive members, such as an urethane-based adhesive or a silicon-based adhesive, are provided on both surfaces of the first pad portion 211 so that one surface of the first pad portion 211 may be attached to the attachment surface 115, and the other surface thereof may be attached to the mesh member 220. The adhesives on both surfaces of the first pad portion 211 may be the same material, or may be different materials. For example, one surface of the first pad portion 211, which is to be attached to the attachment surface 115 may be provided with a silicon-based adhesive, and the other surface thereof, which is to be attached to the mesh member 220, may be provided with an urethane-based adhesive. According to an embodiment of the present invention, the first pad portion 211 may have a thickness of about 0.9~1.5 mm.

The second pad portion 212 may have a specific thickness, and may have the through openings 214 corresponding to the electrodes 131, 132, and 133 set forth above. Adhesive members, such as an urethane-based adhesive or a silicon-based adhesive, may be provided on both surfaces of the second pad portion 212 so that one surface of the second pad portion 212 may be attached to the mesh member 220, and the other surface thereof may be attached to the user's body. The adhesives at both surfaces of the second pad portion 212 may be the same material, or may be different materials. For example, one surface of the second pad portion 212, which is to be attached to the mesh member 220 may be provided with an urethane-based adhesive, and the other surface thereof, which is to be attached to the user's body, may be provided with a silicon-based adhesive. The second pad portion 212 may have a smaller thickness than that of the first pad portion 211. As described above, the second pad portion 212 may have only the through openings 214 to thereby cover the receiving openings 213 of the first pad portion 211. The mesh member 220 having a conductive gel member 230, as described later, is interposed between the first pad portion 211 and the second pad portion 212.

The pad member 210, according to an embodiment of the present invention, may be made of a flexible material to be transformed according to the transformation of the measuring device 100 while it is attached to the attachment surface 115 of the measuring device 100. For example, the pad member 210 may be made of felt, silicon, or rubber.

The conductive gel member 230 fills the through openings 214 to make contact with the first to third electrodes 131, 132, and 133, and the user skin. The gel member is conductive, so it may be used as a means for extending the range of the electrode. That is, the conductive gel member 230 makes contact with the body to detect the biometric information signal, so that the range of the biometric signal received by the electrodes from the user can be extended.

The mesh member 220 is positioned between the first pad portion 211 and the second pad portion 212. The mesh member 220 may prevent the conductive gel member 230 from popping out of the through opening 214 in the pad member 210 when the wearable biometric information measurement device is attached to the user's body. More specifically, when detaching the pad member 210 that has been attached to the user's body, a part of or all of the conductive gel member 230 may adhere to the skin of the user. The mesh member 220 may prevent the conductive gel member 230 from leaving the through opening 214.

The conductive gel members 230 set forth above may be filled into the through openings 214 in a state in which the first pad portion 211, the mesh member 220, and the second pad portion 212 are stacked. The conductive gel members 230 then may be dried.

Although the mesh member 220 is illustrated as interposed between the first pad portion 211 and the second pad portion 212 in the present embodiment, its position is not limited thereto. According to structure, the mesh member 220 may be positioned on the upper surface or the lower surface of the pad member 210, or may be omitted. The configuration of the mesh member may be variously modified and changed.

The film covers 250 are attached to both surfaces of the pad member 210 to protect the adhesive members provided on both sides of the pad member 210. The film covers 250 may be removed when the pad member 210 is attached to the measuring device 100 and the user's body. Accordingly, the disposable gel pad 200 may be carried with the film covers 250 attached to the both surfaces of the pad member 210. In order to attach the disposable gel pad 200 to the measuring device 100 and the user's body, after the user removes the film covers 250 on both surfaces of the pad member 210, the user may attach the disposable gel pad 200 to the measuring device 100, and may attach the pad member 210 to the user's body (see FIG. 17).

Figure 15:
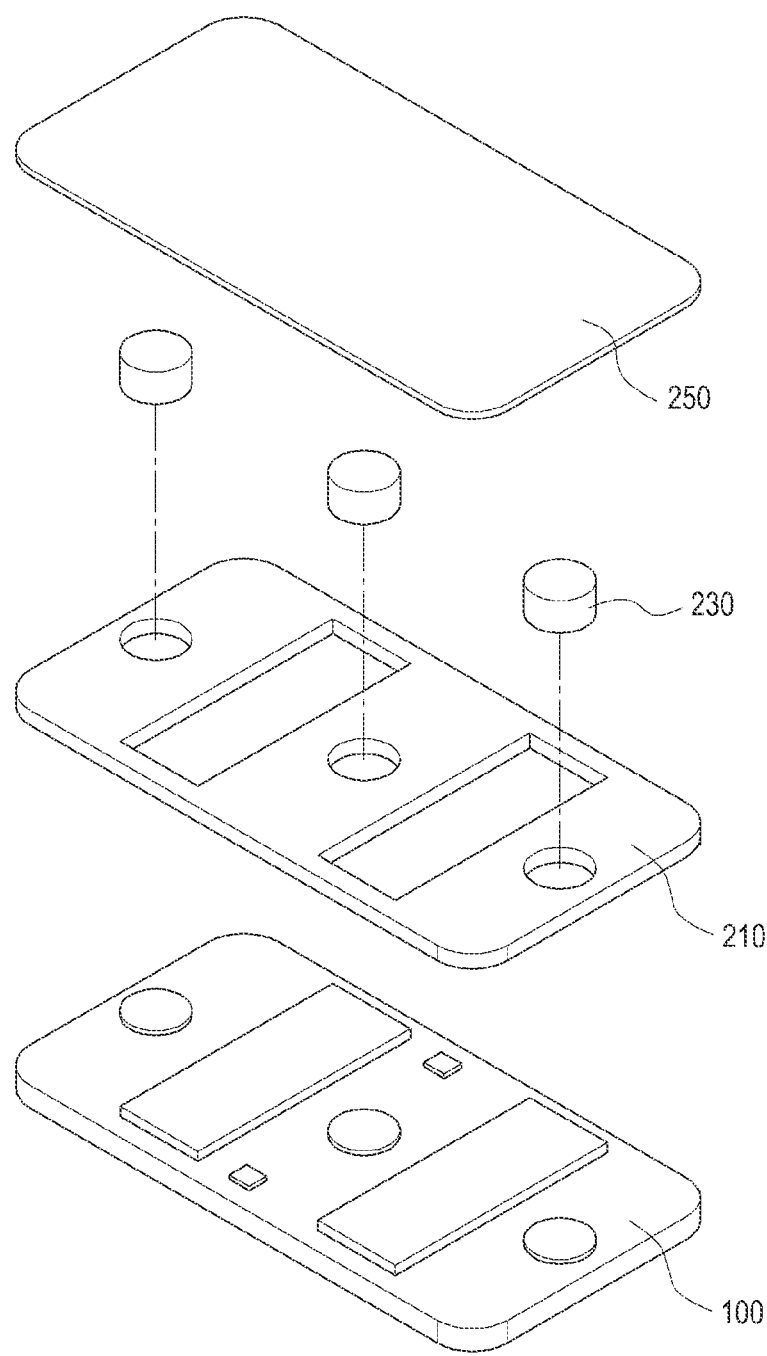
FIG. 15 is a diagram illustrating an exploded perspective view of a disposable gel pad in a wearable biometric information measurement device, according to an embodiment of the present invention.

FIG. 15 is a diagram illustrating a disposable gel pad in the wearable biometric information measurement device, according to an embodiment of the present invention.

Referring to FIG. 15, the disposable gel pad 200 differs from the disposable gel pad of FIG. 14 in the structure of the pad member 210 and the provision of the mesh member. More specifically, the disposable gel pad 200, according to an embodiment of the present invention, includes the pad member 210, and the conductive gel member 230. The pad member 210, according to an embodiment of the present invention, may be configured as a single member. More specifically, the pad member 210 has the receiving openings 213 in which the first and the second protruding surfaces 115b and 115c are accepted, and the through openings 214 filled with the conductive gel members 230. Although the receiving openings 213 penetrate through the pad member 210 in the present embodiment of the disclosure, the receiving openings 213 may be formed as recesses that have an upper surface and an lower opening to receive the first and the second protruding surfaces 115b and 115c.

Adhesive members, such as an urethane-based adhesive or a silicon-based adhesive, may be provided on both surfaces of the pad member 210 so that the pad member 210 can be attached to the attachment surface 115 and the user's body. The pad member 210 may have a specific thickness, and may be made of felt. As described above, since the adhesive members are provided on both surfaces of the pad member 210, according to an embodiment of the present invention, the film covers 250 may be provided on both sides of the pad member 210 before it is attached to the measuring device 100 and the user's body. Therefore, the disposable gel pad 200 may be carried with the film covers 250 attached to both surfaces thereof. When the user wishes to attach the disposable gel pad 200 to the measuring device 100 and the user's body, the film covers 250 on both surfaces of the pad member 210 may be removed to be thereby attached to the attachment surface 115 and the user's body, respectively (see FIG. 17).

Figure 16:
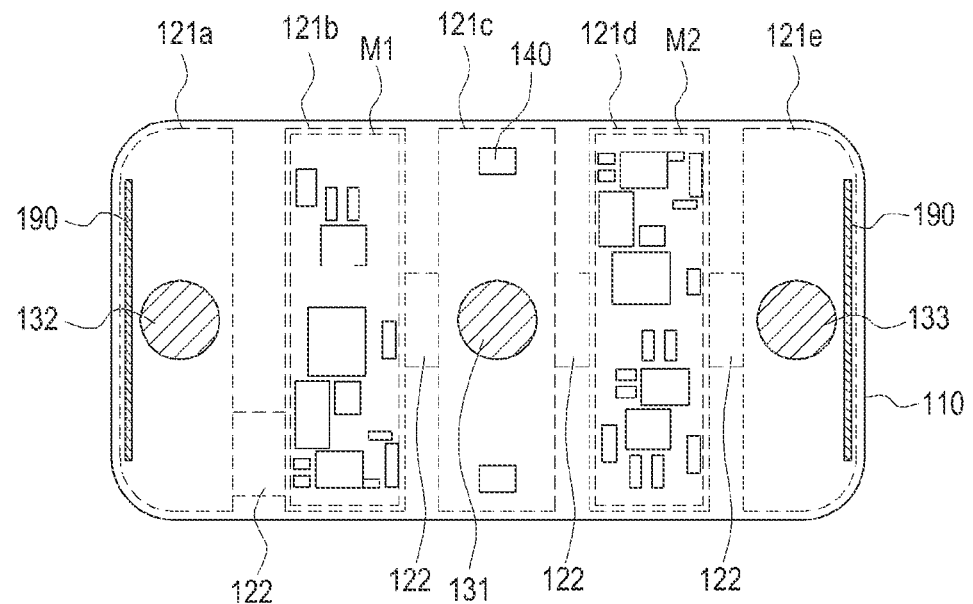
FIG. 16 is a diagram illustrating a substrate unit having perception sensors on one side thereof in a wearable biometric information measurement device, according to an embodiment of the present invention.

FIG. 16 is a diagram illustrating a substrate unit having perception sensors on one surface thereof in the wearable biometric information measurement device, according to an embodiment of the present invention.

Referring to FIG. 16, perception sensors 190 are provided on the first surface S1 of the substrate unit 120, which detect the attachment of the disposable gel pad 200. Detected values of the perception sensors 190 may be applied to the controller 170, and the controller 170 may turn on/off the switching unit 125 according to the detected values of the perception sensors 190. The perception sensors 190 may be configured as at least one of a proximity sensor, a infrared sensor, or a pressure sensor.

The perception sensors 190 may be exposed through the attachment surface 115, so that when the disposable gel pad 200 is attached to the attachment surface 115, the perception sensors 190 may detect the attachment of the disposable gel pad 200. A detected value of the perception sensors 190 may be applied to the controller 170, and the controller 170 turns on/off the measuring device 100 according to the detected value. Therefore, the measuring device 100 may be controlled to be turned on/off according to the detected value even without manipulation of the switching unit 125 by the user.

Figure 17:
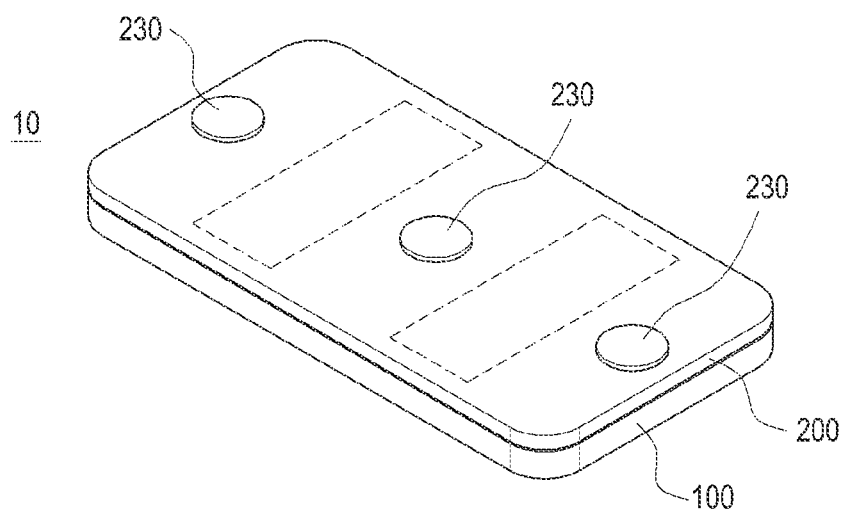
FIG. 17 is a diagram illustrating a measuring device, to which a disposable gel pad has been coupled, in a wearable biometric information measurement device, according to an embodiment of the present invention.
Figure 18:
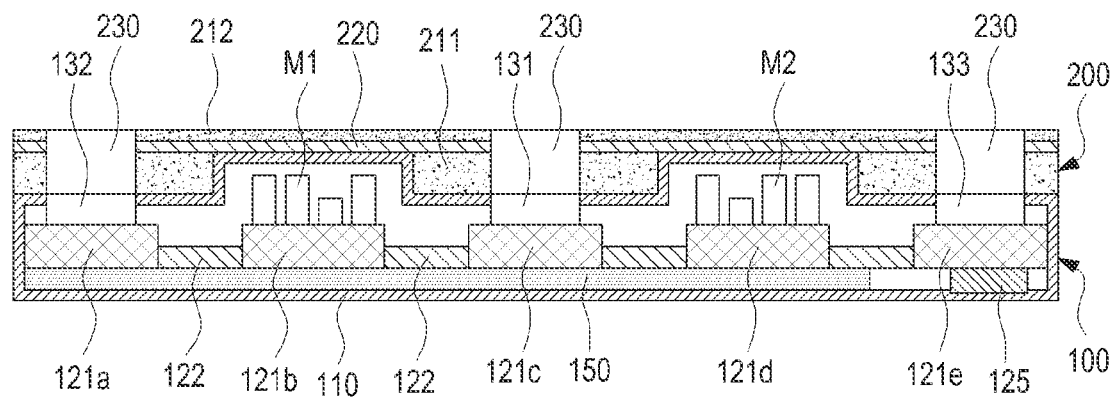
FIG. 18 is a diagram illustrating a cross-section of a measuring device, to which a disposable gel pad has been attached, in a wearable biometric information measurement device, according to an embodiment of the present invention.
Figure 19:
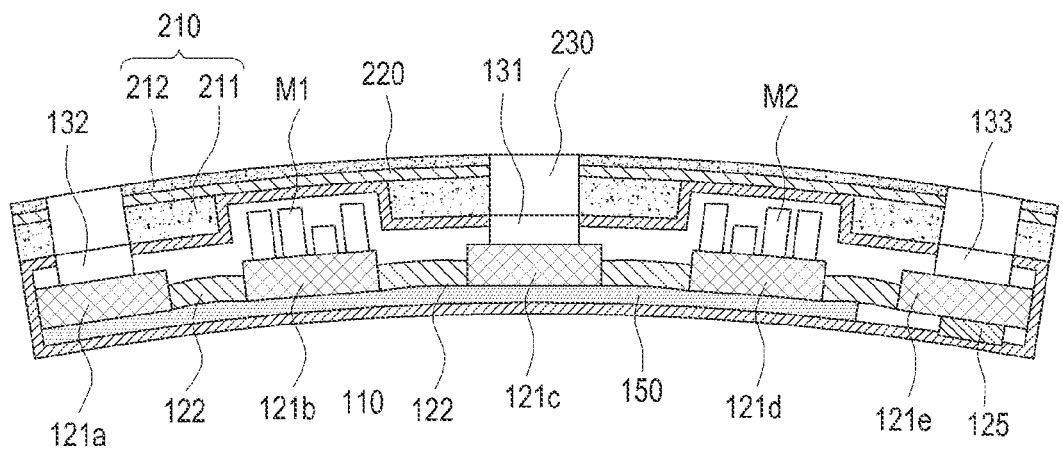
FIG. 19 is a diagram illustrating a cross-section of a measuring device in a bent state, to which a disposable gel pad has been attached, in a wearable biometric information measurement device, according to an embodiment of the present invention.

FIG. 17 is a diagram illustrating a measuring device, to which a disposable gel pad has been coupled, in a wearable biometric information measurement device, according to an embodiment of the present invention. FIG. 18 is a diagram illustrating a cross-section of the measuring device, to which the disposable gel pad has been attached, in the wearable biometric information measurement device, according to one of the various embodiments of the present disclosure. FIG. 19 is a diagram illustrating a cross-section of the measuring device in a bent state, to which the disposable gel pad has been attached, in the wearable biometric information measurement device, according to an embodiment of the present invention.

Referring to FIGS. 17 to 19, the user may attach the disposable gel pad 200 to the measuring device 100 in order to measure the user biometric information signal and the user status information.

More specifically, the film cover 250 on the surface facing the attachment surface 115 of the case 110 is removed, and the pad member 210 is attached to the attachment surface 115 of the case 110 so that the first and the second surfaces 115b and 115c are received by the receiving openings 213 of the pad member 210. When the pad member 210 is attached to the attachment surface 115 of the case 110, the first and the second protruding surfaces 115b and 115c may be inserted into the receiving openings 213, and the conductive gel member 230 in the through opening 214 may make contact with the surfaces of the electrodes 131, 132, and 133. The film cover 250 attached to the upper surface of the pad member 210 that has been attached to the attachment surface 115 of the case 110 may be removed, and the case 110 may be attached to the user's body, based on the marked point 160 of the case 110. At this time, the conductive gel member 230 makes a contact with the user's body through the through opening 214. When the case 110 with the pad member 210 is attached to the user's body, the switching unit 125 on the back surface of the case 110 may be directed towards the front of the user. The user may press the switching unit 125 to drive the measuring device 100. In addition, in the case of adopting the perception sensors 190, when the disposable gel pad 200 is attached to the attachment surface 115, even without manipulation of the switching unit 125 by the user, the perception sensors 190 may detect the attachment of the disposable gel pad 200, and may drive the measuring device 100 according to the detected values of the perception sensors 190.

In addition, the case 110 is flexible, and a plurality of substrates 121a, 121b, 121c, 121d, and 121e are connected by the flexible circuit boards 122. Furthermore, the disposable gel pad 200 is made of a deformable material, such as felt. Therefore, the wearable biometric information measurement device 10 can be attached to a curved body part, and can be transformed according to the movement of the user wearing the wearable biometric information measurement device 10, to thereby minimize the user inconvenience.

Figure 22:
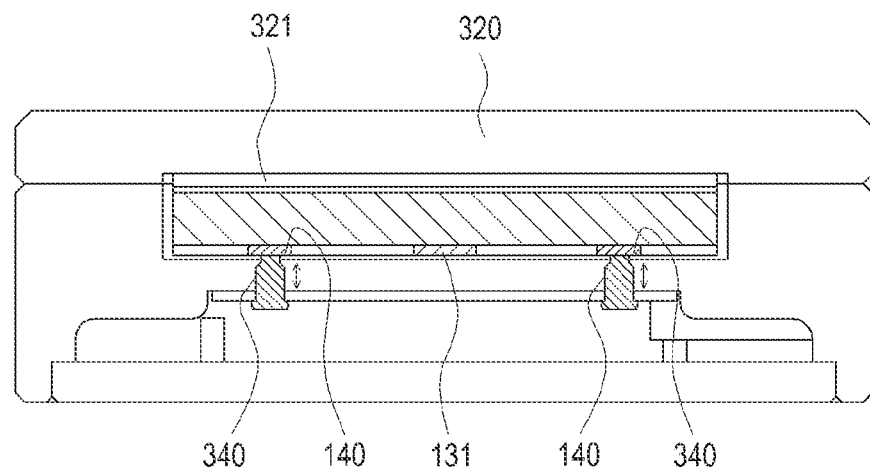
FIG. 22 is a diagram illustrating a widthwise cross-section of a charging module that has accepted a measuring device therein, in a wearable biometric information measurement device, according to an embodiment of the present invention.
Figure 23:
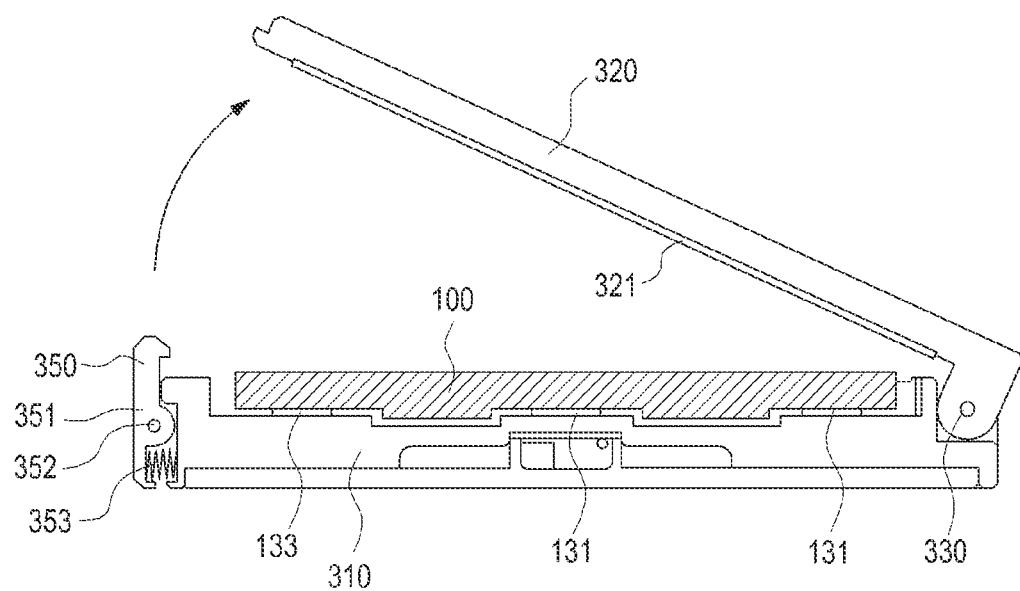
FIG. 23 is a diagram illustrating a charging module in an open state, which has accepted a measuring device therein, in a wearable biometric information measurement device, according to an embodiment of the present disclosure.
Figure 24:
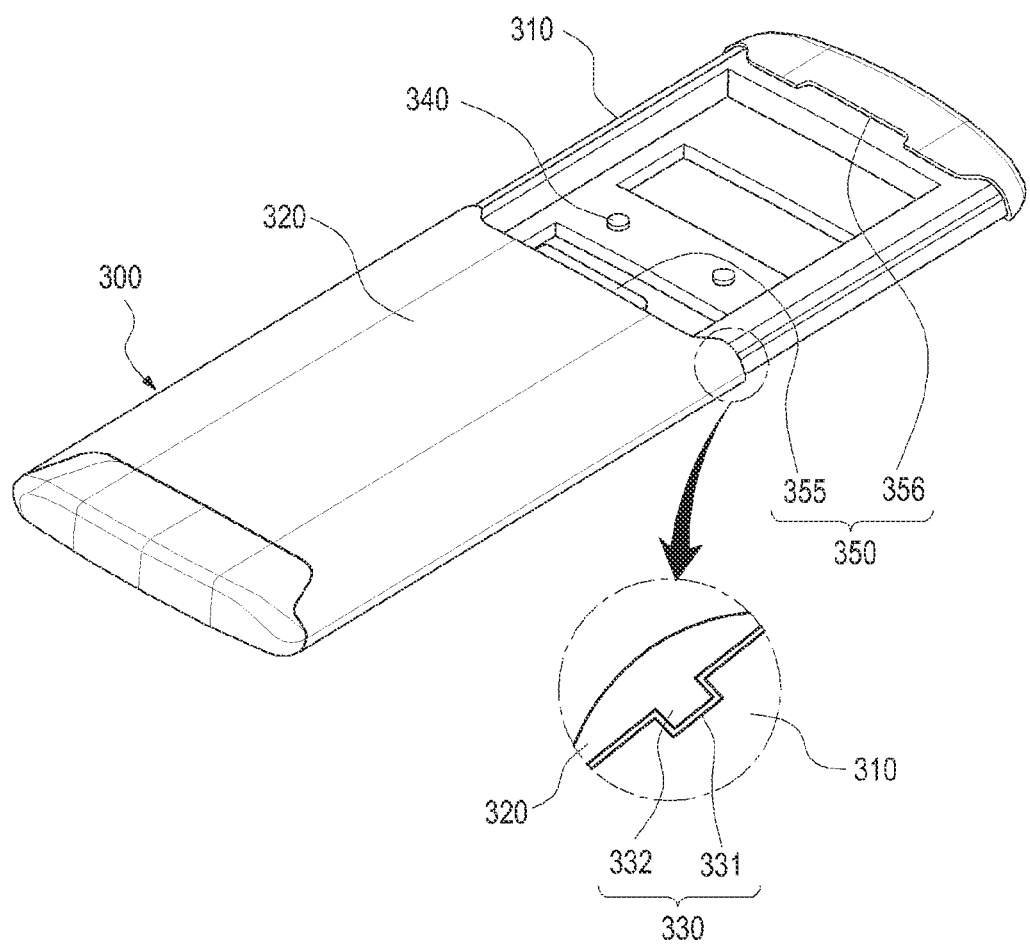
FIG. 24 is a diagram illustrating a charging module in a wearable biometric information measurement device, according to an embodiment of the present invention.
Figure 25:
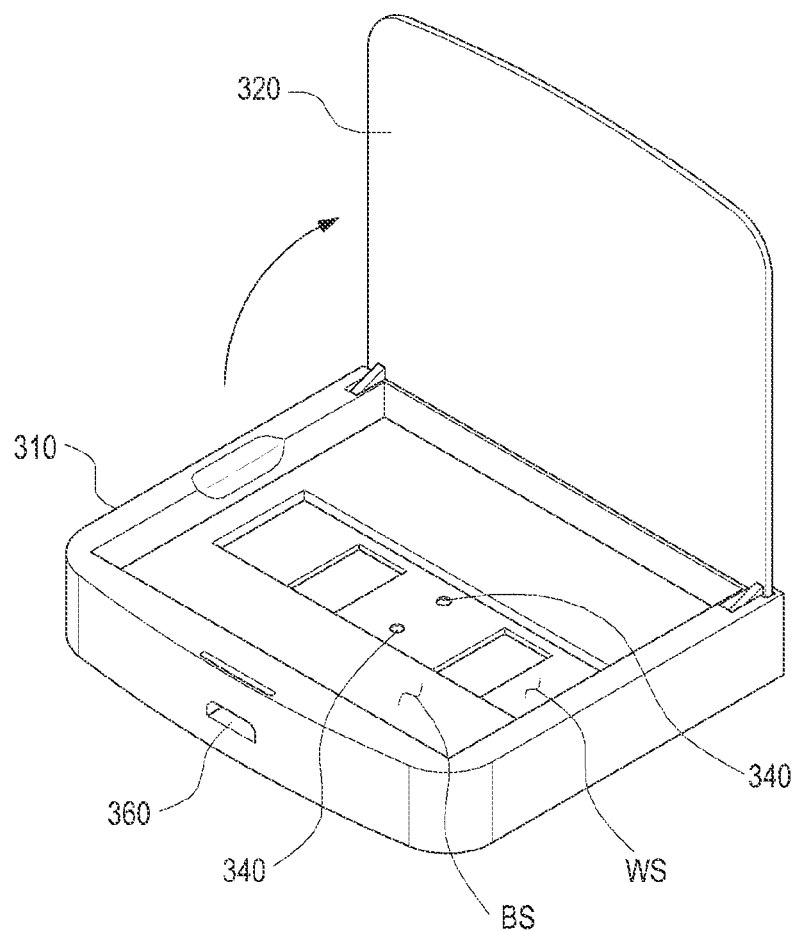
FIG. 25 is a diagram illustrating a charging module in a wearable biometric information measurement device, according to an embodiment of the present invention.

The measuring device 100, according to an embodiment of the present invention, may adopt a separate charging module 300 for charging the internal battery 150 provided in the case 110. FIGS. 20 to 23 show a first embodiment of the charging module, FIG. 24 shows a second embodiment of the charging module, and FIG. 25 shows a third embodiment of the charging module.

Figure 20:
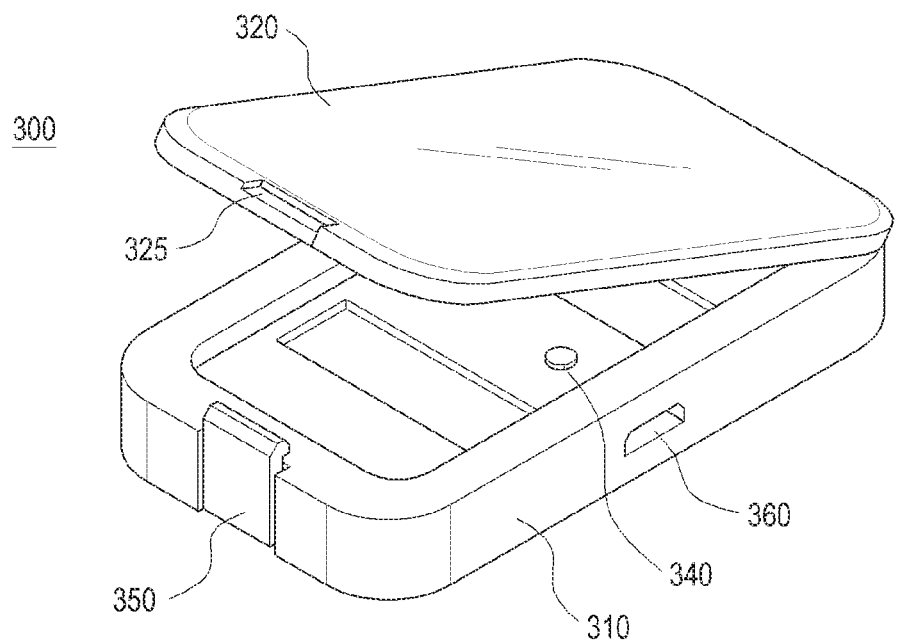
FIG. 20 is a diagram illustrating a charging module for charging a measuring device, in a wearable biometric information measurement device, according to an embodiment of the present invention.
Figure 21:
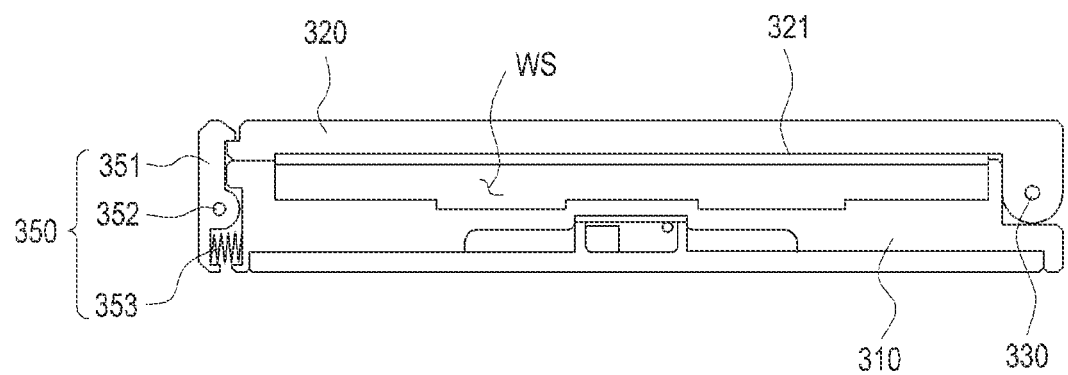
FIG. 21 is a diagram illustrating a lengthwise cross-section of a charging module that has accepted a measuring device therein, in a wearable biometric information measurement device, according to an embodiment of the present invention.

FIG. 20 is a diagram illustrating a charging module for charging the measuring device, in the wearable biometric information measurement device, according to an embodiment of the present invention. FIG. 21 is a diagram illustrating a lengthwise sectional view of the charging module that has accepted the measuring device therein, in the wearable biometric information measurement device, according to an embodiment of the present invention. FIG. 22 is a diagram illustrating a widthwise sectional view of the charging module that has accepted the measuring device therein, in the wearable biometric information measurement device, according to an embodiment of the present invention. FIG. 23 is a diagram illustrating a charging module in an open state, which has accepted the measuring device therein, in the wearable biometric information measurement device, according to an embodiment of the present invention.

Referring to FIGS. 20 to 23, the measuring device 100, according to an embodiment of the present invention, may adopt a separate charging module 300 for charging the internal battery 150 provided in the measuring device 100. The connection ports 140, which electrically connect with external devices for transmission/reception of data, or the charging module 300 for charging the internal battery 150, may be provided on the attachment surface 115 of the measuring device 100. According to an embodiment of the present invention, the connection ports 140 may be configured as charging connection ports 140 that are electrically connected with the charging module 300. The charging connection ports 140, according to an embodiment of the present invention, are provided on the first surface S1 of the substrate unit 120 to be exposed through the attachment surface 115. More specifically, the charging connection ports 140 are positioned on the upper and lower portions of the first electrode 131 on the first surface S1 in the third substrate 121c so that the charging connection ports 140 are exposed through the attachment surface 115 between the first protruding surface 115b and the second protruding surface 115c. The charging connection ports 140 are electrically connected with the internal battery 150 provided on the back of the substrate unit 120 to charge the internal battery 150 when the connection pins 340 of the charging module 300 make contact with the charging connection ports 140.

The charging module 300 includes a body 310, a lid 320, a coupling member 330, and a fastener 350. The body 310 has an accepting space WS for accepting the case 110 of the measuring device 100. Connection pins 340 are formed to protrude from the bottom surface of the accepting space WS, and may be configured as being elastically pressed. When the case 110 is accepted in the accepting space WS with the attachment surface 115 facing the bottom surface of the accepting space WS, the attachment surface 115 of the case 110 comes in contact with the bottom surface of the accepting space WS, and the charging connection ports 140 make contact with the connection pins 340 for the electrical connection. The connection pins 340 may be elastically pressed by the case 110, so the reliability of contact between the connection pins 340 and the charging connection ports 140 can be enhanced. In addition, the body 310 may further include a cable connection unit 360 for a connection with external cables, e.g., a power cable, or a data cable, which is formed on the side of the body 310. For example, when the power cable is connected to the cable connection unit 360, the internal battery 150 in the case 110 may be charged, and when the data cable is connected to the cable connection unit 360, the user biometric information or the user status information detected by the measuring device 100 can be transmitted to the external devices through the data cable.

The lid 320 is configured to be moved to open from or close over the accepting space WS. For example, the lid 320 may rotate or slide with respect to the body 310 to thereby open from or close over the accepting space WS. The charging module 300 may further include a pressing member 321 for pressing the measuring device 100 accepted in the accepting space WS. That is, after the case 110 is accepted in the accepting space WS, when the lid 320 covers the accepting space WS, the pressing member 321 may press the case 110. Accordingly, the charging connection ports 140 press the connection pins 340 to thereby enhance the reliability of the contact between the connection pins 340 and the charging connection ports 140. The pressing member 321 may be made of elastic materials, such as sponge, rubber, or silicon.

The coupling member 330 may couple the body 310 and the lid 320 so that the lid 320 can rotate or slide with respect to the body 310.

In the embodiment illustrated in FIGS. 20-23, the lid 320 rotates with respect to the body 310, and the coupling member 330 may be configured as a hinge unit to allow the lid 320 to rotate on the body 310.

The hinge unit may include a side hinge arm provided on the body 310, and a center hinge arm that is provided on the lid 320 to fit into the side hinge arm to rotate. In addition, elements, such as cams, shafts, or springs, may be further provided in order to configure an automatic opening/closing function by an external force.

The fastener 350 is configured to fix the lid 320 in a closed state, with respect to the body 310. The fastener 350 may lock or unlock a locking groove 325 of the lid 320. The fastener 350 may lock the locking groove 325 of the lid 320 so that the lid 320 may fix or press the case 110 accepted in the accepting space WS. In addition, in the case of automatically opening/closing the lid 320, the accepting space WS may be opened or closed according to the locking or unlocking of the fastener. The fastener 350, according to an embodiment of the present invention, may have a hooking member 351, a pin 352, and an elastic member 353.

The hooking member 351 may be provided on the side of the body 310 to rotate about the pin 352. The hooking member 351 may rotate so that the end of the hooking member 351 fits into the locking groove 325 of the lid 320 or is released from the same. The end of the hooking member 351 may be shaped into a hook that locks or unlocks the locking groove 325 of the lid 320.

The pin 352 may be provided between the hooking member 351 and the body 310. The pin 352 is a rotation axis about which the hooking member 351 rotates on the body 310.

The elastic member 353 may be provided between the other end of the hooking member 351 and the body 310 to provide an elastic force to the hooking member 351 for its rotation about the pin 352. The elastic member 353, according to an embodiment of the present invention, may be a spring.

The locking groove 325 may be formed on the edge of the lid 320 to correspond to the end of the hooking member 351. The locking groove 325 may be locked or unlocked by the hook of the hooking member 351.

When pressing the other end of the hooking member 351, the elastic member 353 between the other end of the hooking member 351 and the body 310 is pressed, so that the hooking member 351 may be rotated about the pin 352. As the hooking member 351 rotates, the end of the hooking member 351 may escape from the locking groove 325, so that the lid 320 can be rotated to open the accepting space WS of the body 310. The hooking member 351 may be rotated by the elastic member to return to the original position.

After the lid 320 is opened, the measuring device 100 may be placed in the accepting space WS of the charging module 300 to charge the same. When the measuring device 100 is placed with the attachment surface 115 in contact with the bottom surface of the accepting space WS, the charging connection ports 140 may make contact with the connection pins 340. In such a state, if the lid 320 that has been opened is rotated again to make the end of the hooking member 351 fit into the locking groove 325, the lid 320 may be fixed to cover the body 310, and the pressing member 321 provided on the inner surface of the lid 320 may press the case 110. With the case 110 elastically pressed by the elastic member 321, the charging connection ports 140 may press the connection pins 340 to thereby maintain the contact between them, so the reliability of contact between the charging connection port 140 and the connection pin 340 can be enhanced.

FIG. 24 is a diagram illustrating a charging module in the wearable biometric information measurement device, according to an embodiment of the present invention.

Referring to FIG. 24, the charging module 300, according to an embodiment of the present invention, is differs from that of FIGS. 20-23 in the operation and the connection of the lid 320 for opening and closing the accepting space WS.

The lid 320 is configured to slide on the body 310 to open or close the accepting space WS. The coupling unit 330, is configured as a sliding module to slidably connect the lid 320 to the body 310.

More specifically, the sliding module, according to an embodiment of the present invention, includes a rail portion 331 and a guide portion 332. The rail portion 331 is formed on the side of the body 310 to guide the sliding of the guide portion 332. The guide portion 332 is formed at both sides of the lid 320 to correspond to the rail portion 331 of the body 310, and is accepted by the rail portion 331 to slide along the rail portion 331.

The fastener 350, according to an embodiment of the present invention, includes a locking hook 355, and an insertion portion 356. The locking hook 355 is formed to protrude from one side of the lid 320, and is received by the insertion portion 356 according to the sliding of the lid 320 to be thereby locked or unlocked.

The insertion portion 356 may be configured so that the locking hook 355 is inserted into the insertion portion 356 to be fixed with the accepting space WS closed by the lid 320.

Accordingly, when the user pushes the lid 320 on the body 310 in order to charge the measuring device 100, the guide portion 332 slides along the rail portion 331 so that the lid 320 slides on the body 310 to thereby open the accepting space WS. When the case 110 is placed in the accepting space WS to allow the attachment surface 115 of the case 110 to make contact with the bottom surface of the accepting space WS, the charging connection ports 140 are connected with the connection pins 340. When the lid 320 slides to the original position, the lid 320 slides to close the accepting space WS with the measuring device 100 placed therein.

FIG. 25 is a diagram illustrating a charging module in the wearable biometric information measurement device, according to embodiment of the present invention.

Referring to FIG. 25, the charging module 300 is provided in a battery charger of the other electronic device 400. More specifically, the charging module 300 is provided in the battery charger of the external electronic device 400 that interworks with the wearable biometric information measurement device 10. The body 310 may include the first accepting space WS where the measuring device 100 is placed to be charged, and the second accepting space BS where a battery of the electronic device 400 is placed to be charged.

The first accepting space WS is formed at a predetermined position in the second accepting space BS, and the first accepting space WS is formed to be recessed as much as the size of the measuring device 100 in the bottom surface of the second accepting space BS. The connection pins 340 make contact with the charging connection ports 140 to thereby charge the internal battery of the measuring device 100.

Charging pins may be formed on the second accepting space BS, which make contact with the charging connection pins 340 to charge the battery.

With the first and the second accepting spaces WS and BS, the measuring device 100 and the battery may be simultaneously charged. On the contrary, only the measuring device 100 may be placed in the first accepting space WS to be charged, or only the battery may be placed in the second accepting space BS to be charged.

The lid 320 is movably provided on the body 310 to open or close the first accepting space WS and the second accepting space BS. The lid 320 is shown to be rotatably coupled to the body 310, but the lid 320 may be slidably coupled to the body 310 to open and close the first accepting space WS and the second accepting space BS, as described above. The coupling unit 330 may be configured in the same manner as the embodiments set forth above.

In addition, when the measuring device 100 is placed in the first accepting space WS to be charged, a pressing member provided on the inner surface of the lid 320 may press the attachment surface 115 against the bottom surface of the first accepting space WS so that the charging connection ports 140 and the connection pins 340 can make a tight contact with each other.

Figure 26:
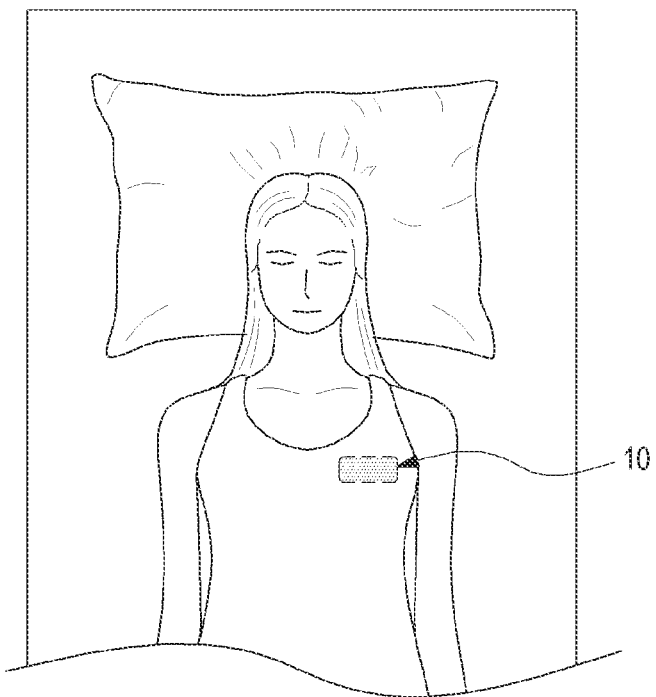
FIG. 26 is a diagram illustrating a user who is asleep wearing a wearable biometric information measurement device, according to an embodiment of the present invention.
Figure 27:
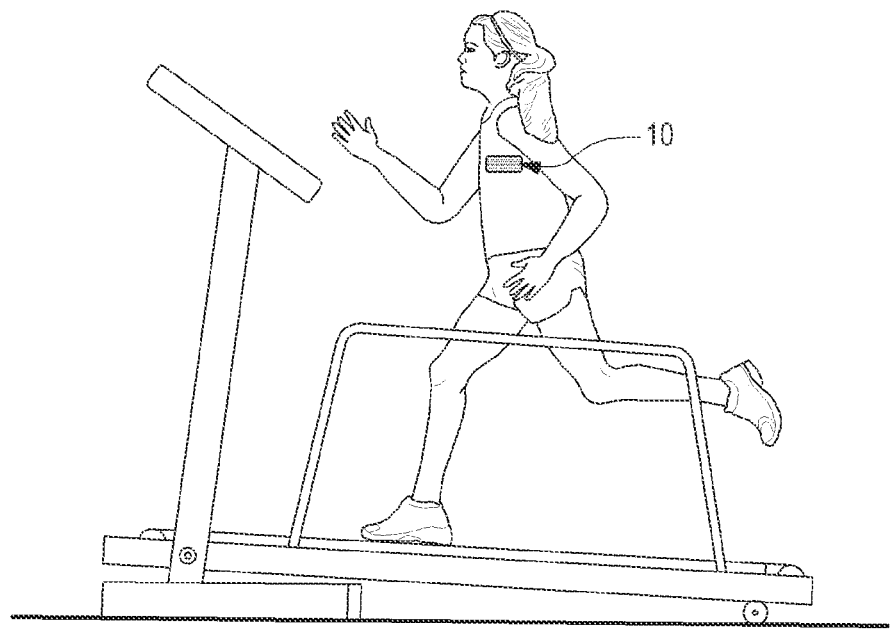
FIG. 27 is a diagram illustrating a user wearing a wearable biometric information measurement device while exercising, according to an embodiment of the present invention.

FIG. 26 is a diagram illustrating a user who is asleep wearing the wearable biometric information measurement device, according to an embodiment of the present invention. FIG. 27 is a diagram illustrating a user wearing the wearable biometric information measurement device while exercising, according to an embodiment of the present invention.

Referring to FIGS. 26 and 27, the user can wear the wearable biometric information measurement device 10 at all times. For example, as shown in FIG. 26, when the user sleeps with the wearable biometric information measurement device 10 attached to the chest of the user, the wearable biometric information measurement device 10 may detect the biometric information, such as sleep stages, a breathing rate per minute, sleep patterns, or sleep postures, and the user physical activity information.

In addition, as shown in FIG. 27, when the user exercises with the wearable biometric information measurement device 10 attached to the chest of the user, the wearable biometric information measurement device 10 may detect biometric information, such as the number of steps, an exercise speed, calorie information, a heart rate, blood pressure, temperature, or humidity, or the user status, such as the user physical activity information.

Hereinafter, the biometric signal information and the user status, such as the user physical environment information, which are detected according to the user circumstance, are described with reference to FIGS. 28 and 29.

Figure 28:
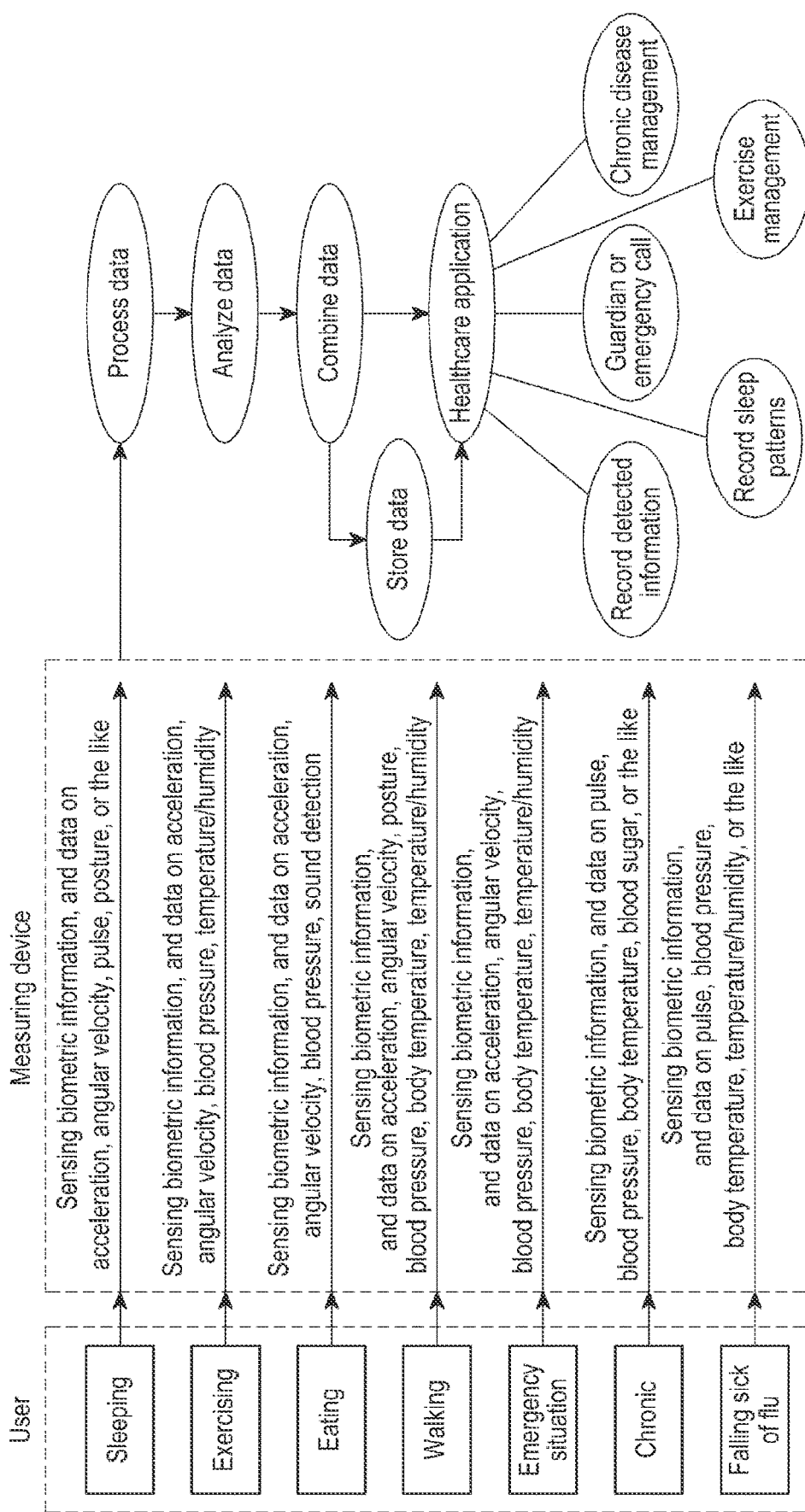
FIG. 28 is a diagram illustrating a diagram for providing a healthcare service through a wearable biometric information measurement device, according to an embodiment of the present invention.

FIG. 28 is a diagram illustrating the providing of a healthcare service through the wearable biometric information measurement device, according to an embodiment of the present invention.

Referring to FIG. 28, the user may wear the wearable biometric information measurement device 10 twenty-four hours a day. Therefore, the user biometric information and the user status information according to the lifestyle may be detected in real time, 24 hours a day. That is, the wearable biometric information measurement device 10 may detect when the user is sleeping, exercising, walking, eating, in emergency situations, such as falling, fainting, or tripping, falling sick of flu or body aches, a change in the physiological status of the user who has a chronic disease, or the like, through the biometric information signals and user physical environment information signals. That is, the biometric information signals may be detected through the electrodes 131, 132, and 133, and the user physical environment information signals may be detected through the detecting sensors, according to the condition.

The data signals, such as the biometric information signals and the user physical environment information signals, may be processed through the biometric information measurement modules "A". In addition, the user status may be analyzed according to circumstances by analyzing the data. Furthermore, the analyzed data may be combined and accumulated to be compared with pre-stored data so that a data table can be obtained to show the accurate biometric information or the user status.

In addition, the user's health may be taken care of through the combined and accumulated data. That is, chronic diseases and the sleeping status may be managed, and the amount of exercising may be managed according to the accumulated data on the user biometric information or the user information in exercising. In addition, emergency situations related to the user activities can be dealt with to thereby provide an improved healthcare service.

Figure 29:
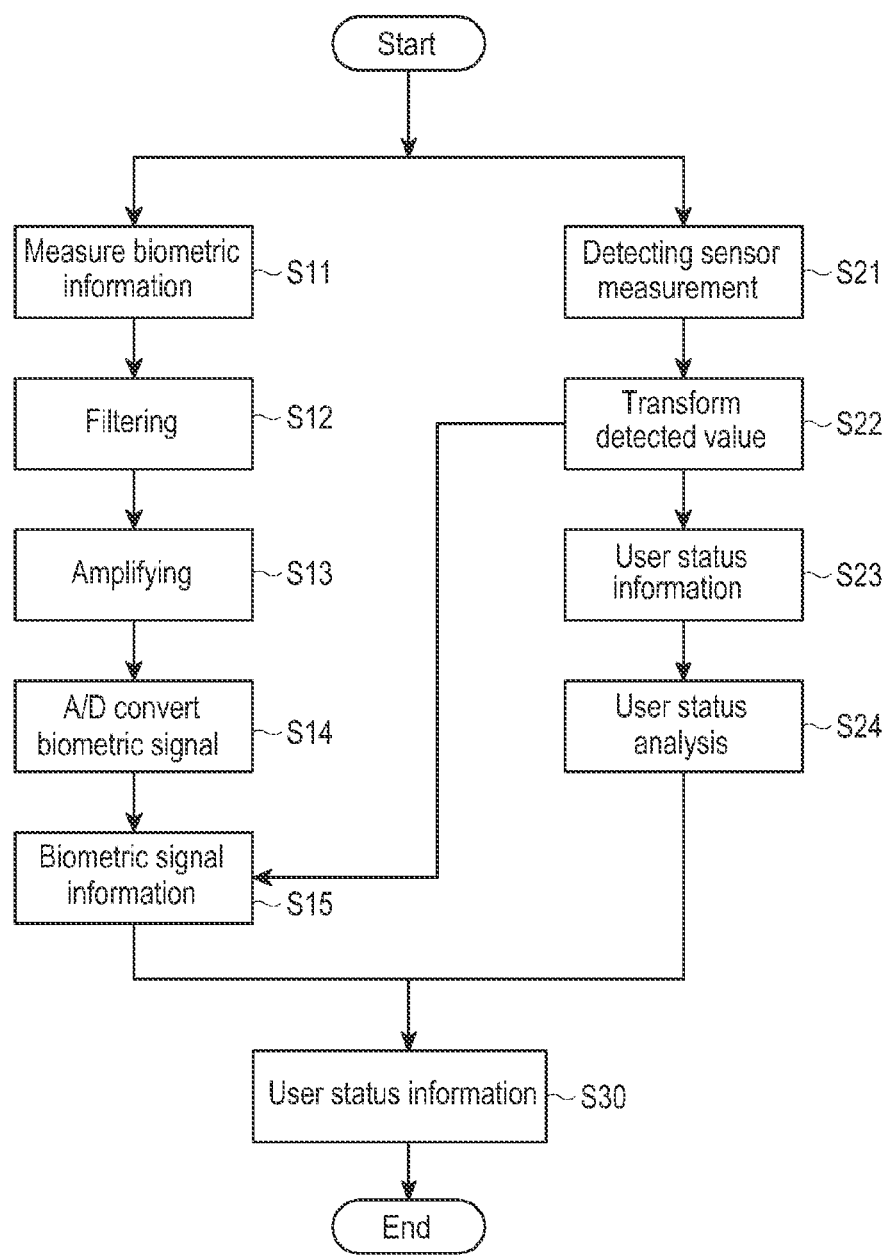
FIG. 29 is a flowchart illustrating a method for detecting the biometric signals and the user status in a wearable biometric information measurement device, according to an embodiment of the present invention.

FIG. 29 is a flowchart illustrating a method for detecting biometric signals and the user status in the wearable biometric information measurement device, according to an embodiment of the present invention.

Referring to FIG. 29, when the user attaches the wearable biometric information measurement device 10 to his or her body and turns on the measuring device 100, the biometric information measurement modules "A", such as the electrodes 131, 132, and 133, or the detecting sensors, detect the user biometric signals, and the user status, such as the user physical activity information, in steps S11 and S21.

That is, the biometric information signals, such as an ECG, are measured through the electrodes, in step S11.

The measured data is filtered, in step S12, is amplified, in step S13, and is A/D-converted, in step S14 by the analog front-end processing module, so that the user biometric signal information is detected, in step (S15).

Separately, the user physical activity information is detected through the detecting sensors, in step S21. The detected values of the detecting sensors are transformed into data on the biometric information signals or the user status information, in step S22. The transformed data is used for obtaining and analyzing the user status information, in steps S23 and S24, or is combined with the data value of the biometric information signal, in step S15 to detect more accurate user's health information, compared with the analysis obtained using only the biometric information signal, in step S30.

For example, a biometric signal measurement value, which is measured while the user is sleeping, may be filtered, amplified, and transformed into data.

Furthermore, various values may be detected according to the user sleeping status through an acceleration sensor, an angular velocity sensor, a sound detecting sensor, a temperature/humidity sensor, and the detected values may be transformed into data on the user status, such as sleeping status, sleep postures, sleep patterns, sleep stages, or sleep positions. Such data may be combined with the detected values of the biometric signal information to thereby provide the user status information. Separately, the detected values of the detecting sensors may be transformed into data on the user status to be stored, and the data may be compared with the accumulated data to thereby detect the user status information.

As described above, the detected values of the detecting sensors may be transformed into data to be stored and accumulated as the user environment information, and the stored data may be compared with data measured in real time to thereby analyze the user environment information more accurately. In addition, the data values detected by the detecting sensors may be combined with the biometric signal information to thereby detect more accurate user's health information than the analysis based on only the biometric information signals.

That is, the wearable biometric information measurement device 10, according to various embodiments of the present disclosure, may be attached to the user's body, and may detect the biometric signals all the time so that the user physical activities, such as sleeping, eating, exercising, or relaxing, can be measured. In addition, the measured biometric signals and the user physical activities may be simultaneously recorded and stored, so a change in the biometric signal may be analyzed according to the user physical activities. In addition, the biometric signals may be analyzed based on the user physical activities to thereby provide more accurate healthcare service suitable for the user.

Figure 30:
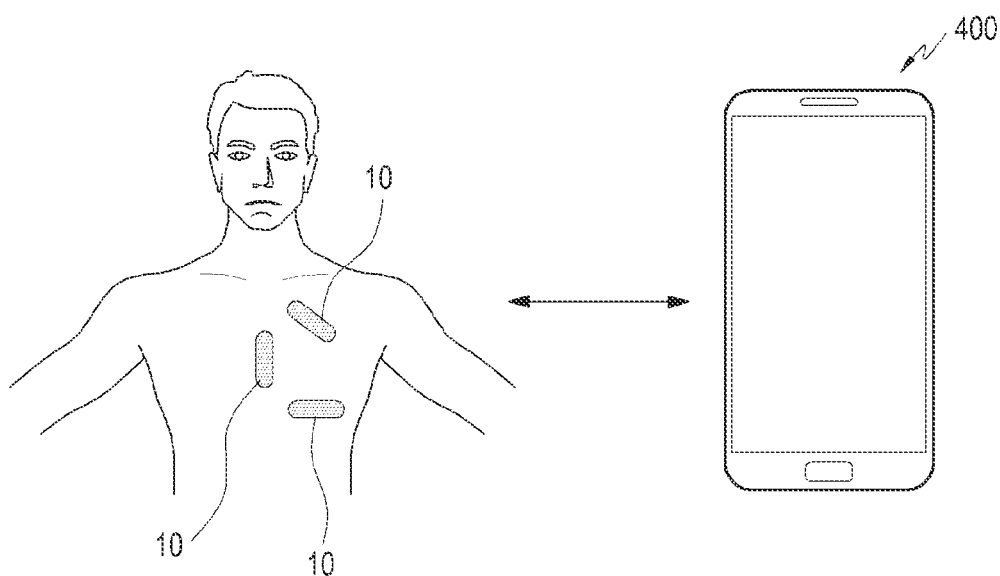
FIG. 30 is a diagram illustrating proper attachment positions of a wearable biometric information measurement device and interworks thereof with an external electronic device, according to an embodiment of the present invention.
Figure 33:
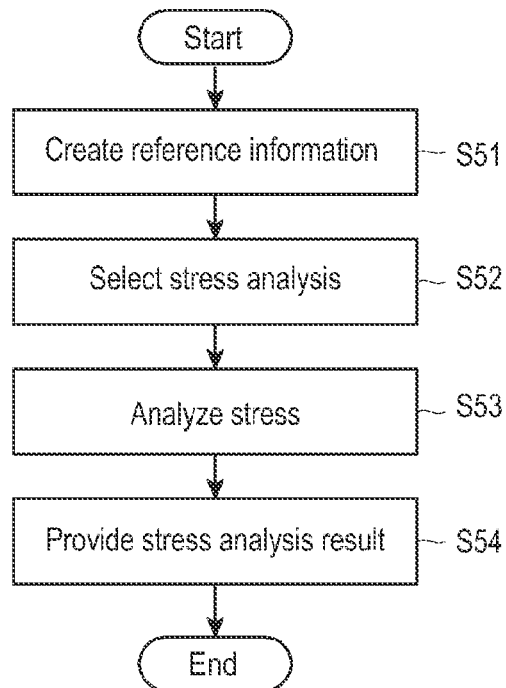
FIG. 33 is a flowchart illustrating a stress analyzing method, according to an embodiment of the present invention.

FIG. 30 is a diagram illustrating a wearable biometric information measurement device that interworks with an external electronic device, according to an embodiment of the present invention. FIG. 31 is a diagram illustrating the displaying of ECG signal information detected through a wearable biometric information measurement device on an external electronic device 400, according to an embodiment of the present invention. FIG. 32 is a diagram illustrating the displaying of a user stress index on an external electronic device 400 through the signal information detected by a wearable biometric information measurement device 10, according to an embodiment of the present invention. FIG. 33 is a flowchart illustrating a stress analyzing method, according to an embodiment of the present invention.

Referring to FIGS. 30 to 33, when the user attaches the wearable biometric information measurement device 10 to the his or her chest or around the same, the wearable biometric information measurement device 10 may measure, analyze, or store the user biometric information, and the user environment information. Furthermore, the external electronic device 400, such as a smart phone, may be provided, which interworks with the wearable biometric information measurement device 10 attached to the user's body in wired/wireless communication, and receives the detected data of the wearable biometric information measurement device to thereby analyze, combine, store, or display the same.

The electronic device 400 may analyze, display, or store the data on the user biometric information and physical activity information using a health mode, and may be provided with various health-related services according to the user setup (see FIG. 9). The electronic device 400 may receive the biometric information and the user status information, which are transmitted and received by the wearable biometric information measurement device 10 to thereby provide various health-related services.

The health mode may be divided into a measurement driving mode (hereinafter, referred to as a "measurement mode") and a management driving mode (hereinafter, referred to as a "management mode") according to the attachment of the wearable biometric information measurement device to the user's body. More specifically, in a state in which the wearable biometric information measurement device 10 is attached to the body, the user may select the measurement mode or the management mode, and in a state in which the wearable biometric information measurement device 10 is not attached to the body, the device may be driven in the management mode.

In addition, the health mode may create individual user profiles, based on the data measured by the wearable biometric information measurement device 10. For example, the individual user profiles may be created based on the ECG data measured by the biometric information measurement modules "A." The individual healthcare can be made using the individual user profiles. An example is set forth below in which two users are using the biometric information measurement modules. For example, when the wearable biometric information measurement device 10 is attached to a user "A," an individual user profile for the user "A" may be created through the biometric information measured from the user "A." In addition, when the wearable biometric information measurement device 10 is attached to a user "B," an individual user profile for the user "B" may be created through the biometric information measured from the user "B." Afterwards, when the user "A" attaches the wearable biometric information measurement device 10 to the body, the biometric information that is measured in real time is compared with the stored individual user profile to identify that the biometric information belongs to the user "A" and to execute the health mode for the user "A."

For example, when the health mode for the user "A" is executed, the user sleeping status, sleep periods, sleep stages, or sleep patterns may be determined based on the biometric information, such as an ECG, or the environment information, such as movement, on the user "A", which are detected by the biometric information measurement modules "A" or the electrodes. In addition, the detecting sensor, such as the sound detecting sensor, may detect whether or not the user is eating, and may record and manage the eating time in the health mode, based on the detected values. Furthermore, the detecting sensor, such as the acceleration sensor, may measure the movement of the user, and may analyze the user exercise status and postures through the movement data in the health mode. In addition, through the ECG values detected by the electrodes, a stress index or a breathing rate of the user, as described later, as well as the ECG information may be measured. In addition, the user's health information, such as sleep apnea that is hardly recognized by the user, may be detected according to the measurement of the breathing rate while sleeping. In addition, the detecting sensor, such as the temperature/humidity sensor, may measure the temperature and the humidity of the environment of the user to thereby analyze the same and provide necessary information in the health mode. The health information on a heartbeat differential rate, a stress index, or sleep stages of the user may be analyzed in the health mode according to the data measured by the biometric information measurement modules "A," or the user activity status or the user environment status may be detected to be displayed in the health mode.

As described above, the health mode may be divided into the measurement mode and the management mode.

In the measurement mode, the data on the user biometric information and the user status, which are detected in the wearable biometric information measurement device 10, may be transmitted in real time to the electronic device, and may allow the electronic device to analyze, display, or store the same. For example, as shown in FIG. 31, the detected values measured in the wearable biometric information measurement device 10 may be transmitted to the electronic device in real time, and the heart rate of the user may be displayed in real time according to the execution of the measurement mode in the electronic device. The heart rate may be transformed into data to be stored with the date and time, and the data information may be analyzed to show the user's health status in real time.

For example, the ECG information detected by the wearable biometric information measurement device 10 may be displayed as an ECG graph in the health mode, i.e., a measurement mode as shown in FIG. 31. In addition, as will be described in greater detail below, the measured data values, such as the ECG data, may be stored and analyzed to be displayed in the management mode as shown in FIG. 32, so that various pieces of information, such as an analysis on the user's physical condition and a caring method thereof, may be provided according to the user's physical condition.

In the management mode, the user biometric information or the user environment information may be analyzed through the measured or stored data, and the user activity information or patterns thereof may be detected based on the analyzed data values to allow the user to recognize his or her health status or lifestyle and to take care of their physical condition and make a healthcare plan. For example, the user biometric information data and the user environment information data, which are measured by the wearable biometric information measurement device may be stored in real time according to the user, the date, or the like. The user can identify or recognize the user's health status or lifestyle according to the period and the health status.

The user may identify the user's health status and lifestyle through the stored data, and various health-related services necessary for the user may be provided based on the same.

For example, the measurement of a stress index through the measured ECG values of the user is shown in FIGS. 32 and 33. The user may execute the health mode in which the electronic device 400 is connected with the wearable biometric information measurement device. When the wearable biometric information measurement device is attached to the user's body, the user biometric information and the user environment status may be detected in real time so that the detected values are transmitted to the electronic device to be stored in addition to the pre-stored data. The user may select the management mode of the health management mode and may select information that he or she wishes to know. As shown in the example, if the user wishes to know the stress index, the user may select the detection of the stress index.

The selection of the stress index requires a reference to analyze the stress index. Thus, with respect to FIG. 33, the reference related to the stress index may be created through the detected pre-stored data or the real time data, in step S51. For example, the user may create a reference for the stress index as "very low", based on the stored data measured in a state in which the user is relaxed. According to this, the references of a plurality of stress indexes may be created, for example, as "very low," "low," "normal," "high," and "very high." The user may select the ECG values measured in real time or the necessary data to detect the stress index, in step S52. The controller provided in the electronic device 400 may receive and analyze the selected data, in step S53, and may display the analyzed data on the screen, in step S54.

In addition, the user may perform a preliminary check for measuring the stress index more accurately. For example, in measuring the stress index, the user may select a score for the user's feeling or the user's condition with respect to various questions related to the stress index to create variable data that is to be used for basic information data in determining the stress index. Thus, in the management mode executed by the user, the variable data and the ECG data may be combined, analyzed, and compared with the reference values so that user stress values or the degree of the stress may be analyzed. The analyzed stress index may be displayed through a display of the electronic device to allow the user to recognize the stress information. In addition, separate health information on stress-releasing methods or the user status depending on the stress may be provided based on the stress index.

Figure 34:
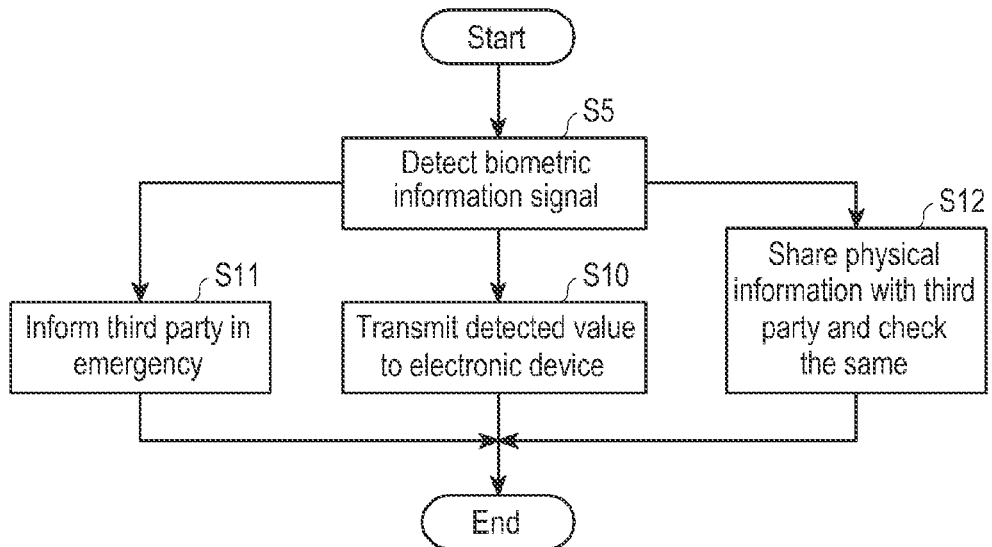
FIG. 34 is a flowchart illustrating detection of health information in an electronic device that has received values detected by a wearable biometric information measurement device, according to an embodiment of the present invention.

FIG. 34 is a flowchart illustrating detection of health information in an electronic device that has received values detected by a wearable biometric information measurement device, according to an embodiment of the present invention.

Referring to FIG. 34, a health status measurement method, according to an embodiment of the present invention, may include a detecting step S5, and a receiving step S10.

In the detecting step S5, the disposable gel pad 200 may be attached to the first surface S1 of the biometric information measurement modules "A" including the substrate unit 120, on which the modules M1 and M2, and the electrodes 131, 132, and 133 are mounted to face the user's body, and the first surface S1 of the disposable gel pad 200 may be attached to the user's body to thereby detect the user biometric information and the user status information.

In the receiving step S10, the data on the biometric information and the user status information detected in the detecting step S5 may be transmitted through the transmitting/receiving module of the wearable biometric information measurement device 10 and the transmitting/receiving module of the electronic device 400.

An emergency signal may be detected in relation to the user's body. That is, if the emergency situation related to the user's body is detected from the biometric information or the user status, for example, when the user has a heart attack or a stroke, or when the user falls down, the wearable biometric information measurement device may detect the emergency information. The emergency information detected by the wearable biometric information measurement device 10 is transmitted to a predetermined third party, in step S11. Therefore, the necessary step for the emergency situation can be taken within a short time to allow the user to escape from the emergency situation. For example, the device may be configured to call "911" in the case of an emergency situation. In addition, the device may be configured to inform a family doctor or relatives in the case of the emergency situation. Thus, when the emergency situation occurs, the family doctor or the relatives may be informed of the same to help the user with the emergency situation.

On the contrary, the wearable biometric information measurement device may be configured to share the user biometric information or the user environment information with the third party so that the detected data may be displayed to the user through a separate electronic device, and the third party may recognize the user biometric information and the user environment information, in step S12. In addition, the family doctor may recognize the user biometric information and user environment information to thereby check the user's health status. In addition, in the case where the user uses the wearable biometric information measurement device, who suffers from chronic diseases, such as asthma, or the user has undergone heart surgery, his family doctor may recognize and check the health information or the health status according to the surgery or the user's condition in real time.

Figure 35:
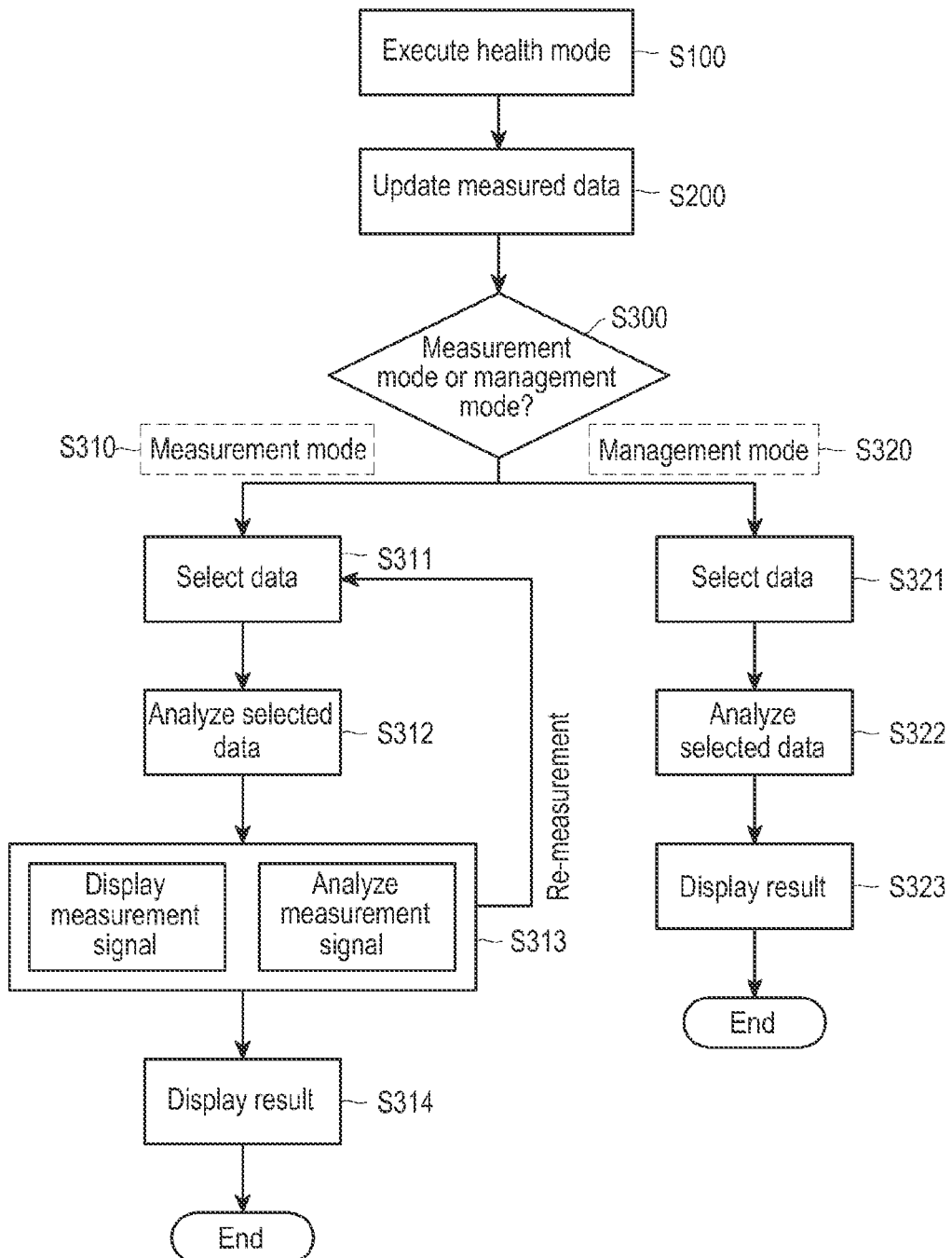
FIG. 35 is a flowchart illustrating a method for measuring the health status through a wearable biometric information measurement device and an electronic device, according to an embodiment of the present invention.

FIG. 35 is a flowchart illustrating a method of measuring the health status through a wearable biometric information measurement device and an electronic device, according to an embodiment of the present invention.

The health mode may be executed based on the detected value that has been received by the electronic device 400 in a driving operation S100.

In the driving operation, the health mode is performed, in which the user's health information may be measured through the information received by the electronic device 400 in the receiving operation, or the user's health may be taken care of through the stored information.

The driving operation executing the health mode in step S100, updating the received information according to the executed health mode in step S200, and selecting one of the measurement mode in which the real time measured information data is displayed, and the management mode in which the information data selected from the stored information is displayed, in steps S300, S310, and S320.

If the measurement mode is selected, first biometric information data (including ECG values detected through the electrodes, values detected through the detecting sensors, and a combination thereof), which is detected in real time through the detecting operation S5 and the receiving operation S10, or the second biometric information data (ECG detected values that have been measured and stored through the electrodes, values detected through the detecting sensors, and a combination thereof) as well as the first biometric information are selected, in step S311. The health information desired by the user, such as a stress index, a heart rate, a heartbeat differential rate, sleep stages, or the like, is analyzed based on the data selected in the measurement mode, in step S312. The analyzed data may be displayed on the screen of the electronic device 400, and data signals of the first biometric information, which are continuously measured in real time, are analyzed, in step 313.

The analyzed data may be stored as the new second biometric information data, and the new first biometric information data continues to be measured to replace the second biometric information in the re-measurement operation. The data of the measurement operation and the data that has been repeatedly measured and analyzed in the re-measurement operation may be displayed as a final result on the screen of the electronic device 400, in step S314.

In addition, if the management mode is selected, some data may be selected from among the final data that has been updated in the second operation, the initial data previously stored, and the data stored between the same, in step S321, and the selected data may be analyzed in step S322. The analyzed data may be displayed as the user's health information, in step S323.

Figure 36:
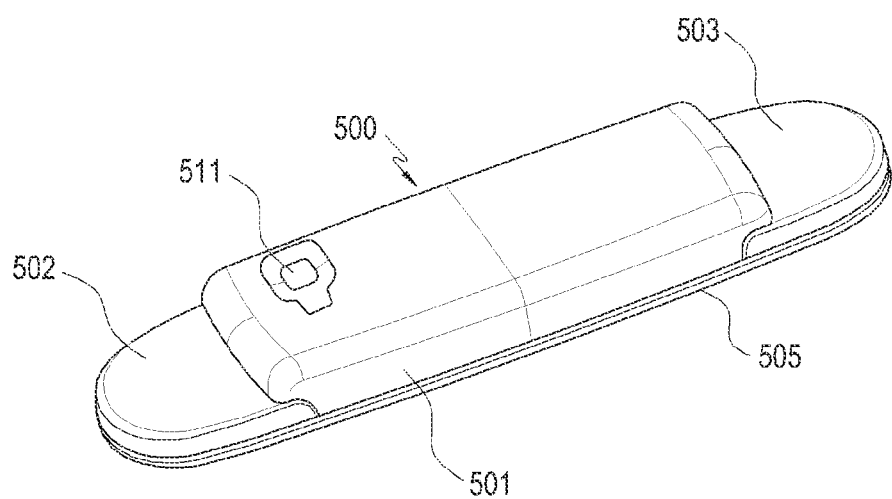
FIG. 36 is a diagram illustrating a perspective view of a biometric information measurement device, according to an embodiment of the present invention.
Figure 37:
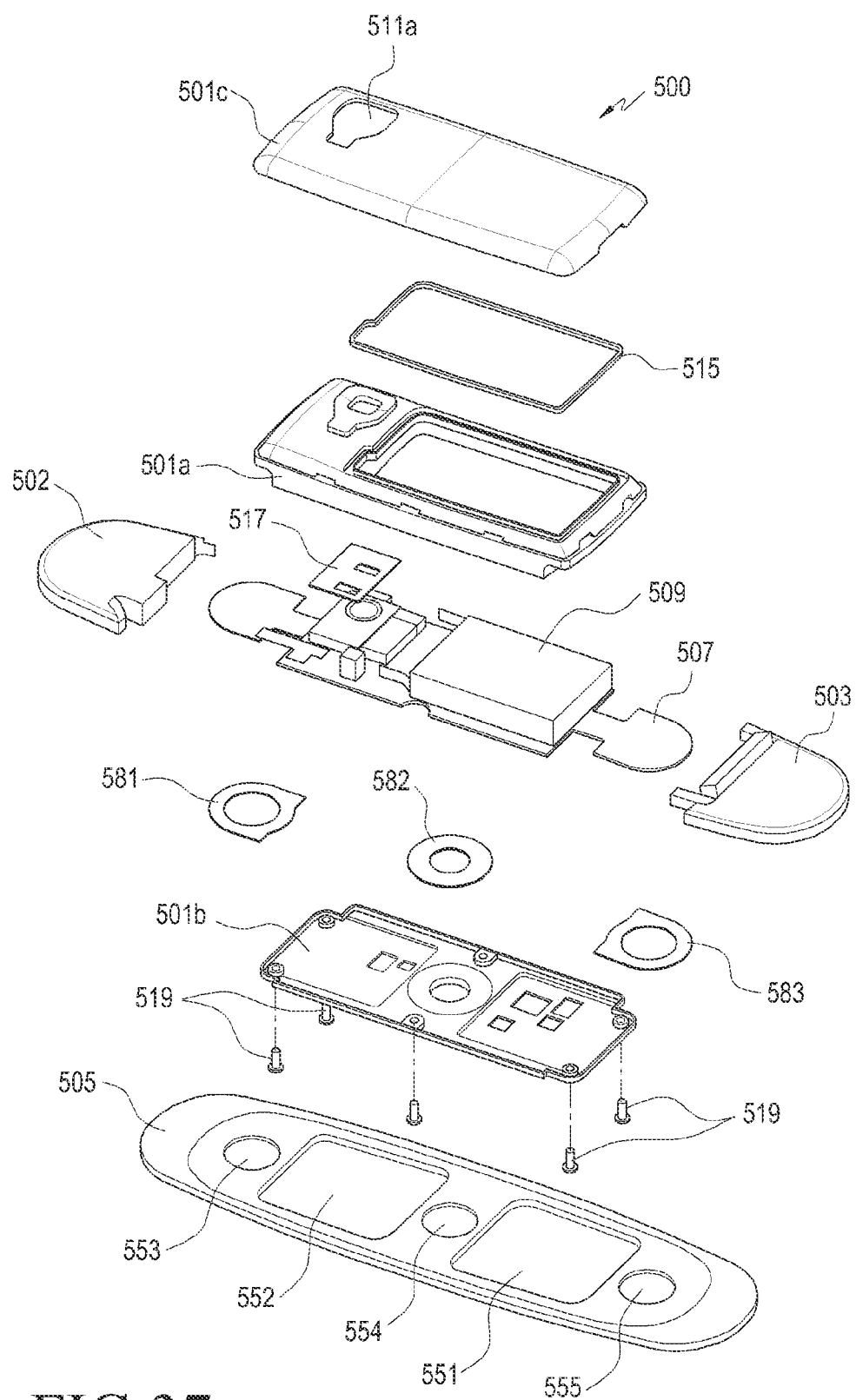
FIG. 37 is a diagram illustrating an exploded perspective view of a biometric information measurement device, according to an embodiment of the present invention.
Figure 38:
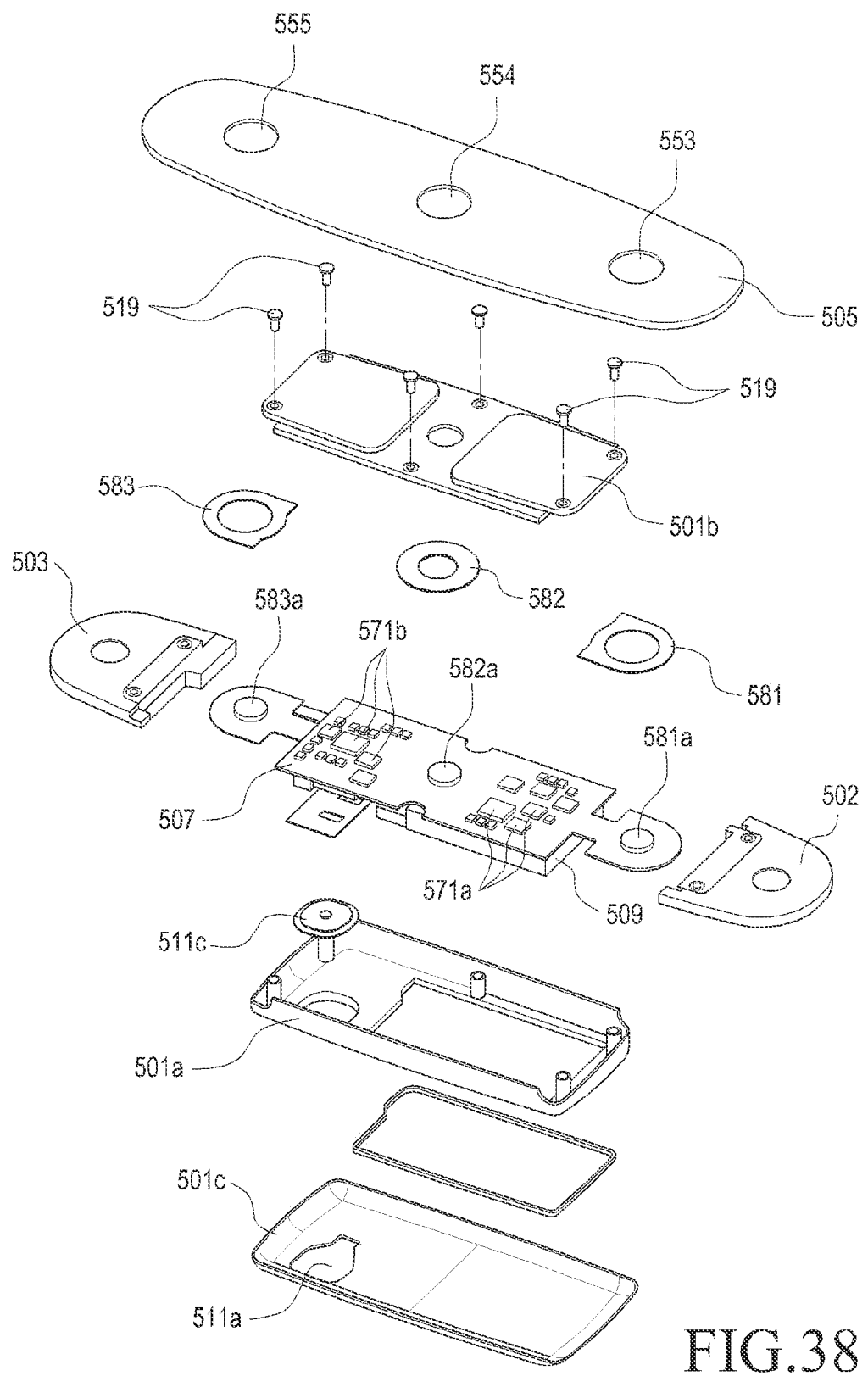
FIG. 38 is a diagram illustrating a second exploded perspective view of a biometric information measurement device, according to an embodiment of the present invention.

FIG. 36 is a diagram illustrating a perspective view of a biometric information measurement device, according to an embodiment of the present invention, and FIG. 37 is a diagram illustrating an exploded perspective view of a biometric information measurement device, according to an embodiment of the present invention. FIG. 38 is a diagram illustrating a second exploded perspective view of a biometric information measurement device, according to an embodiment of the present invention.

Referring to FIGS. 36 to 38, a biometric information measurement device 500, includes a case 501, a substrate unit 507, the first cover member 502, the second cover member 503, an attachment pad 505, and a battery 509.

The case 501 includes a first case 501a that accommodates a portion of the substrate unit 507 and the battery 509, a second case 501b that forms one side of the first case 501a, and a third case 501c that covers an inner space of the first case 501a. In addition, the third case 501c includes a switch opening 511a, and a switch button 511c passes through the switch opening 511a for operation of a dome switch of the substrate unit 507 that turns the substrate unit 507 on or off. In addition, a first sealing member 515 is provided between the first case 501a and the third case 501c. The first sealing member 515 prevents liquid (e.g., water) from permeating between the first case 501a and the third case 501c. In addition, the third case 501c may tightly fit into the first case 501a. Accordingly, the user can detach or couple the first case 501a from or to the third case 501c in order to change the battery 509 in the case 501. In addition, the first case 501a may be coupled to the second case 501b using bolts 519.

The substrate unit 507 includes components 571a and 571b, which are necessary for the operation of the biometric information measurement device, and a plurality of electrodes 581a, 582a, and 583a. For example, the components 571a and 571b, and the plurality of electrodes 581a, 582a, and 583a may be arranged on one side of the substrate unit 507.

The battery 509 is provided on a side of the substrate unit 507 opposite that of the components 571a and 571b and the plurality of electrodes 581a, 582a, and 583a. The battery 509 may be made to be rigid so that the capacity of the electric energy therein may be increased.

In addition, first electrode 581a and the third electrode 583a are provided at both ends of the substrate unit 507, respectively. Both ends of the substrate unit 507 may be flexible to be bent with respect to the center of the substrate unit 507. For example, since both ends of the substrate unit 507 are flexible, the first electrode 581a and the third electrode 583a may be attached to the user's body to correspond to the curvature or movement of the body. In the biometric information measurement device 500, according to an embodiment of the present invention, both ends of the substrate unit 507 are flexible in order to attach the first electrode 581a and the third electrode 583a to the user's body, and the rigid battery 507 is provided in the central area of the substrate unit 507.

The first cover member 502 encloses one end of the substrate unit 507, andthe second cover member 503 encloses the other end of the substrate unit 507. The first and the second cover members 502 and 503 may be made of rubber, or any other flexible material. The first and the second cover members 502 and 503 may protect the both ends of the substrate unit 507, which are exposed to the outside of the case 501.

The biometric information measurement device 500, in accordance with an embodiment of the present invention, includes second sealing members 581, 582, and 583. Each of the second sealing members 581, 582, and 583 wrap a portion of each of the electrodes 581a, 582a, and 583a. Therefore, although the electrodes 581a, 582a, and 583a are exposed to the outside of the case 501, liquid (e.g., water) can be prevented from permeating through the electrode 581a, 582a, and 583a.

The attachment pad 505 is attached to one side of the second case 501b as well as to one side of each of the first and second cover members 502 and 503. In addition, the second case 501b is formed to protrude in order to receive the components 571a and 571b, and the attachment pad 505 includes receiving portions 551 and 552 corresponding to the protrusions of the second case 501b. In addition, the attachment pad 505 includes through-holes 553, 554 and 555 through which the electrodes 581a, 582a, and 583a pass.

As described above, in the biometric information measurement device 500, according to an embodiment of the present invention, since both ends 502 and 503 of the substrate unit 507 can be bent, the electrodes 581a and 583a may be stably attached to the user's body to correspond to the curvature of the body. In addition, the rigid battery may be positioned in the central area of the substrate unit 507 in order to thereby increase the capacity of the battery, considering that the electrodes 581a and 583a are stably attached to the user's body.

Figure 39:
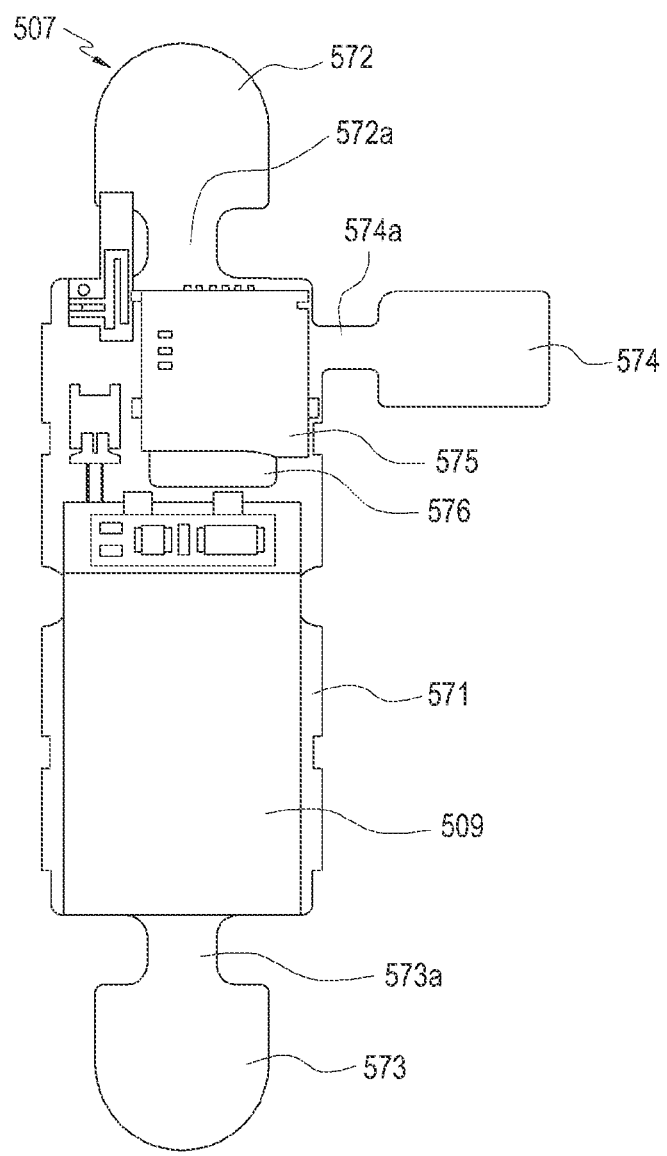
FIG. 39 is a diagram illustrating a front view of a substrate unit and a battery of a biometric information measurement device, according to an embodiment of the present invention.
Figure 40:
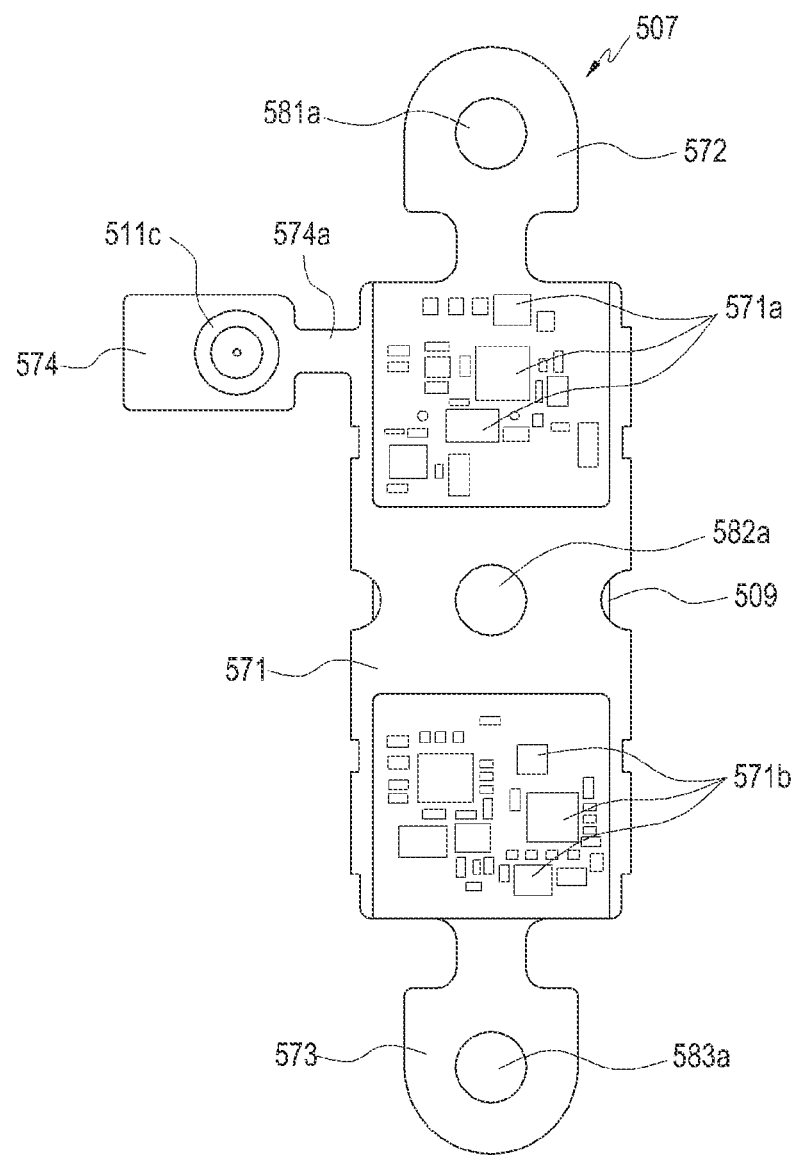
FIG. 40 is a diagram illustrating a back view of a substrate unit and a battery of a biometric information measurement device, according to an embodiment of the present invention.

FIG. 39 is a diagram illustrating a front view of a substrate unit and a battery of a biometric information measurement device, according to an embodiment of the present invention. FIG. 40 is a diagram illustrating a back view of a substrate unit and a battery of a biometric information measurement device, according to an embodiment of the present invention.

Referring to FIGS. 39 and 40, the substrate unit 507 includes a first substrate 571, a second substrate 572, a third substrate 573, a fourth substrate 574, and coupling members 572a, 573a, and 574a between the first, the second, the third, and the fourth substrates 571, 572, 573, and 574.

The coupling members 572a, 573a, and 574a rotatably couple the first, the second, the third, and the fourth substrates 571, 572, 573, and 574 to each other. For example, the coupling members 572a, 573a, and 574a may be bent so that the second, the third, and the fourth substrates 572, 573, and 574 can be coupled to the first substrate 571 to be rotatable with respect thereto.

The first substrate 571 includes the components 571a and 571b necessary for the operation of the biometric information measurement device, the electrode 582a, the battery 509, and a socket 575 that receives a recording medium 576 thereon. For example, the components 571a and 571b, and the electrode 582a are provided on one side of the first substrate 571, and the battery 509 and the socket 575 are provided on the other side of the first substrate 571. In addition, the recording medium 576 may be an SD card or any other storage device for storing the biometric signals. Accordingly, the user can detach the recording medium 576 from the socket and connect the recording medium 576 to another electronic device.

The second and the third substrates 572 and 573 include the electrodes 581a and 583a. Since the coupling members 572a and 573a are flexible, the second and the third substrates 572 and 573 are rotated so that the electrodes 581a and 583a can be attached to the user's body to correspond to the curvature of the body.

The fourth substrate 574 includes a dome switch, and the switch button 511c may be placed on the dome switch. The fourth substrate 574 may be rotated to be placed on the socket 575.

Figure 41:
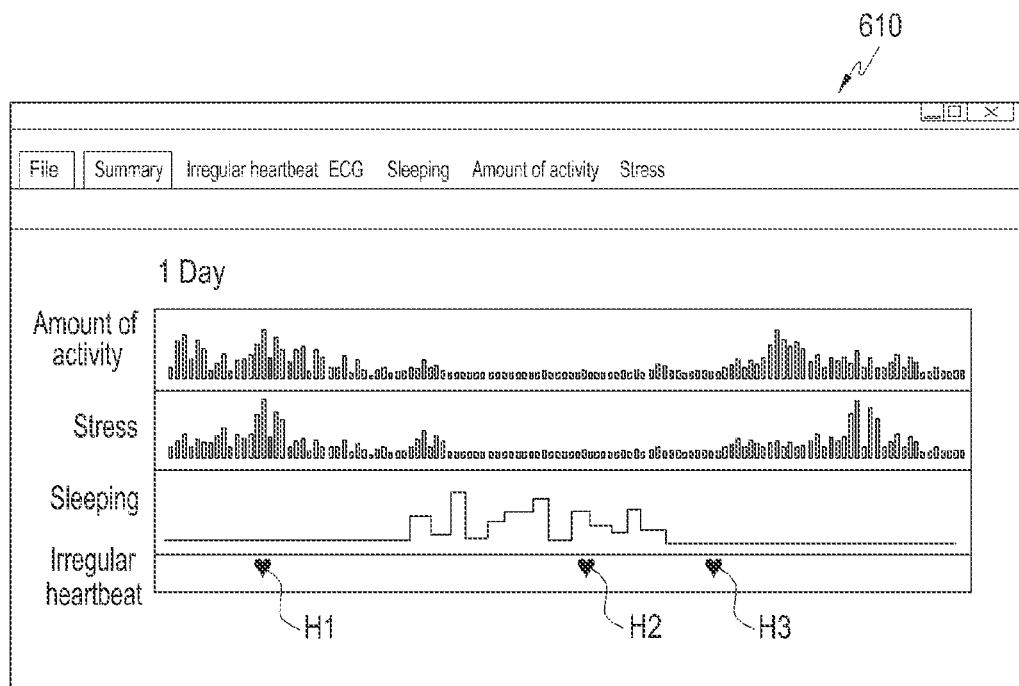
FIG. 41 is a diagram showing that biometric information is displayed in the other electronic device using a recording medium of a biometric information measurement device, according to an embodiment of the present invention.
Figure 42:
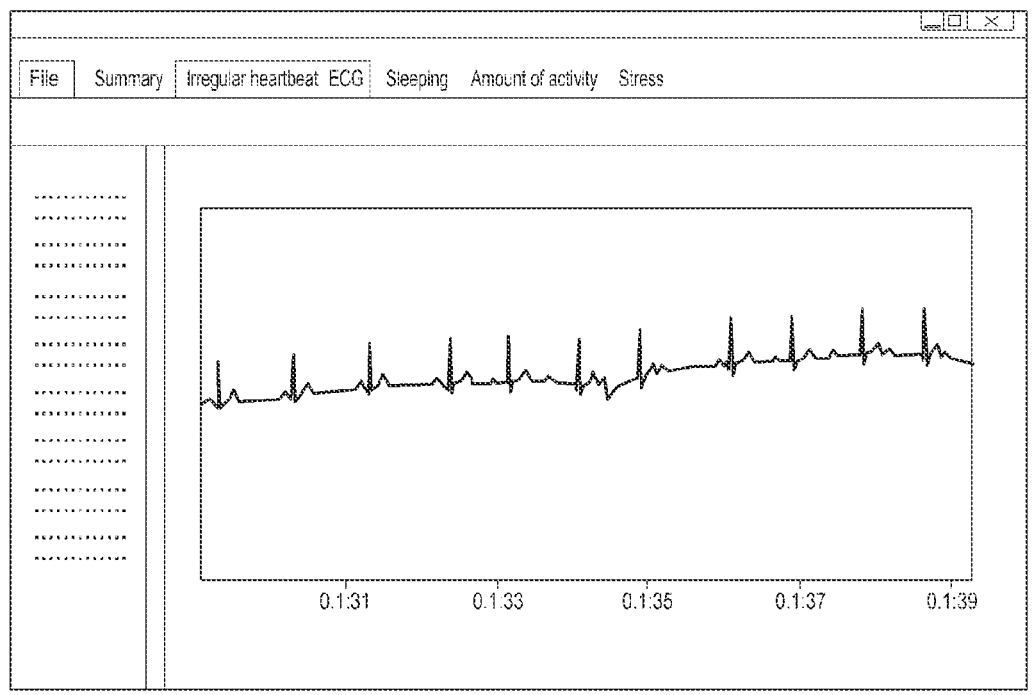
FIG. 42 is a diagram showing the irregular heartbeat of FIG. 41 in detail, according to an embodiment of the present invention.

FIG. 41 is a diagram showing that biometric information is displayed in the other electronic device using a recording medium of a biometric information measurement device, according to an embodiment of the present invention. FIG. 42 is a diagram showing the irregular heartbeat of FIG. 41 in detail, according to an embodiment of the present invention.

The biometric information measurement device (500 of FIG. 36) measures the biometric signals for a long time (e.g., approximately 72 hours) while it is attached to the user's body. The recording medium (576 of FIG. 39) stores the biometric signals, and is then connected to another electronic device. In addition, the biometric signals may be analyzed in another electronic device in order to check the user's health status. Another electronic device may be, for example, a computer or a mobile terminal, which can be connected with the recording medium to analyze the biometric signals.

Referring to FIGS. 41 and 42, another electronic device may include an analysis program 610 for analyzing the biometric signals to display the biometric information, and a display device to display the result of the analysis program.

The analysis program 610 may analyze the biometric signal to thereby display the biometric information. The biometric information may be an amount of activity, a stress index, a sleep index, or an irregular heartbeat index. The amount of activity may be analyzed based on the biometric signal measured by the acceleration sensor, as described in detail above. The amount of activity may be data to identify the calorie consumption and the life style according to the user's physical activity. The stress index may be analyzed based on the heart rate measured by a biometric information measurement modules A and the detecting sensor. For example, the stress index may represent the change in the interval of the heartbeat and may be data to identify the user's stress. The sleep index may be analyzed based on the amount of activity and the heart rate. For example, if the amount of activity measured by the acceleration sensor is zero or is close to zero, the sleep index may be configured as the first setup value to be used as data to show whether or not the user is asleep. In addition, if the heart rate remains constant, the sleep index may be configured as a value greater than the first setup value to be used as data to show whether or not the user is asleep. On the contrary, in the case of an irregular heartbeat, the sleep index may be configured as a value less than the first setup value to be used as data to show whether or not the user is asleep. Furthermore, the irregular heartbeat indexes H1, H2, and H3 may denote a large ECG value, a small ECG value, or an irregular ECG value. When one of the irregular heartbeat indexes H1, H2, and H3 displayed through the display device is selected, the analysis program may display an ECG value 620 per a second/minute of the selected irregular heartbeat index, as shown in FIG. 42. Accordingly, the user or a medical expert determining the user's health may accurately recognize the user's health condition through the biometric information.

While the invention has been shown and described with reference to certain embodiments thereof, it will be understood by those skilled in the art that various changes in form and detail may be made therein without departing from the spirit and scope of the invention as defined by the appended claims.

What is claimed is:

1. A biometric information measurement device, comprising:
    a substrate unit including a plurality of substrates and flexible circuit boards that connect the plurality of substrates, wherein components required for operation of the biometric information measurement device, and electrodes for measuring biometric information, are disposed on a single side of the plurality of substrates; and
    a case encapsulating the substrate unit and having an exterior surface and an interior surface, the exterior surface being attached to an attachment pad for attaching the biometric information measurement device to a user's body, and the interior surface facing the single side of the substrate unit,
    wherein the electrodes are each exposed through respective openings in the case.

2. The device of claim 1, wherein sides of the electrodes are sealed to an interior of the openings.

3. The device of claim 1, wherein:
    the components and the electrodes are individually and alternately arranged on the plurality of substrates.

4. The device of claim 3, wherein the plurality of substrates comprises a first substrate, a second substrate, a third substrate, a fourth substrate, and a fifth substrate, the electrodes are mounted on the first substrate, the third substrate, and the fifth substrate, the components are mounted on the second substrate and the fourth substrate, the second substrate is disposed between the first substrate and the third substrate, and the fourth substrate is disposed between the third substrate and the fifth substrate.

5. The device of claim 4, wherein the electrodes comprise a first electrode disposed on the third substrate, a second electrode disposed on the first substrate, and a third electrode disposed on the fifth substrate, and the biometric information is measured according to a potential difference between the second and third electrodes.

6. The device of claim 5, wherein the respective openings comprise first, second, and third exposure openings through which the first, second, and third electrodes are hermetically exposed, respectively, a first protruding surface is formed between the first and second exposure openings, a second protruding surface is formed between the second and third exposure openings, and the first and the second protruding surfaces have spaces therein, which receive a first component mounted on the second substrate and a second component mounted on the fourth substrate, respectively.

7. The device of claim 6, wherein the attachment pad comprises:
    a pad member having a first adhesive end for attachment to the exterior surface and a second adhesive end for attachment to the user's body, having receiving openings for receiving the first and the second protruding surfaces, and having through openings for receiving the first, second, and third electrodes;
    conductive gel members that are filled in the through openings to make contact between the first, second, and third electrodes and the user's body; and
    a mesh member that is provided within the pad member.

8. The device of claim 7, wherein:
    the pad member comprises a first pad portion having a surface that is attached to the exterior surface;
    the pad member comprises a second pad portion that is connected with the first pad portion and having a surface that is attachable to the user's body; and
    the mesh member is interposed between the first pad portion and the second pad portion.

9. The device of claim 1, further comprising connection ports on the single side of the substrate unit, which are electrically connectable with external ports, and the connection ports are hermetically exposed through the exterior surface.

10. The device of claim 1, wherein a marked point is provided on the case, which indicates an attachment reference point of the case with respect to the user's body.

11. The device of claim 10, further comprising connection ports on the single side of the substrate unit, which are electrically connectable with external ports, and the connection ports are hermetically exposed through the exterior surface.

12. A biometric information measurement device comprising:
    a measuring device comprising:
        a substrate unit on a single side of which components for biometric information measurement and electrodes are mounted, wherein the substrate unit comprises a plurality of substrates and flexible circuit boards that connect the plurality of substrates; and
        a case that encapsulates the substrate unit, through which the electrodes are exposed, and to which a disposable gel pad is attached; and
    the disposable gel pad that is attached to the case, the disposable gel pad comprising:
        a pad member having adhesive for attachment to the case and a user's body, and having first openings corresponding to the components and second openings corresponding to the electrodes;
        conductive gel members that are filled in the second openings to make contact between the electrodes and the user's body; and a mesh member that is provided within the pad member.

13. The device of claim 12, wherein the components and the electrodes are individually and alternately arranged on the plurality of substrates.

14. The device of claim 12, wherein the disposable gel pad comprises a coupling member that is provided on both sides of the mesh member, and that attaches the pad member to the user's body.

15. The device of claim 12, wherein the components measure and analyze health information on a heart rate, a heartbeat differential rate, a stress index, or sleep stages.

* * * * *